United States Patent
Adams et al.

(10) Patent No.: US 11,426,509 B2
(45) Date of Patent: Aug. 30, 2022

(54) SYSTEMS AND METHODS FOR APPLYING REDUCED PRESSURE THERAPY

(71) Applicant: Smith & Nephew, Inc., Memphis, TN (US)

(72) Inventors: Eric Edward Adams, Pittsboro, NC (US); Kevin Bendele, Fort Worth, TX (US); Aaron Michael Husz, Cary, NC (US); David Edward Lee, Durham, NC (US); Felix Clarence Quintanar, Hull (GB); Lee Michael Rush, Saint Petersberg, FL (US); David Ronald Upton, New Hill, NC (US); William Jacob Ward, Apex, NC (US)

(73) Assignee: Smith & Nephew, Inc., Memphis, TN (US)

( * ) Notice: Subject to any disclaimer, the term of this patent is extended or adjusted under 35 U.S.C. 154(b) by 944 days.

(21) Appl. No.: 16/206,860

(22) Filed: Nov. 30, 2018

(65) Prior Publication Data

US 2019/0167867 A1    Jun. 6, 2019

Related U.S. Application Data

(60) Division of application No. 15/895,953, filed on Feb. 13, 2018, now Pat. No. 10,143,785, which is a
(Continued)

(51) Int. Cl.
*A61M 1/00* (2006.01)

(52) U.S. Cl.
CPC ............... *A61M 1/90* (2021.05); *A61M 1/96* (2021.05); *A61M 1/0001* (2013.01);
(Continued)

(58) Field of Classification Search
CPC ...... A61M 2205/14; A61M 1/90; A61M 1/96; A61M 1/60; A61M 2205/15;
(Continued)

(56) References Cited

U.S. PATENT DOCUMENTS

| D239,019 S | 3/1976 | Flinn |
| 4,498,850 A | 2/1985 | Perlov et al. |

(Continued)

FOREIGN PATENT DOCUMENTS

| CN | 103357076 | 10/2013 |
| DE | 10 2015 215165 A1 | 2/2017 |

(Continued)

OTHER PUBLICATIONS

"Battery Charger", Wikipedia, accessed Nov. 9, 2018, in 12 pages. URL: https://web.archive.org/web/20181109005000/https://en.wikipedia.org/wiki/Battery_charger.

(Continued)

*Primary Examiner* — Jessica R Arble
(74) *Attorney, Agent, or Firm* — Knobbe, Martens, Olson and Bear, LLP

(57) ABSTRACT

Embodiments of negative pressure wound therapy systems and methods for operating the systems are disclosed. In some embodiments, a system includes a negative pressure source, a wound dressing configured to be positioned over a wound, and optionally a canister configured to store fluid aspirated from the wound. The negative pressure source, wound dressing, and canister (when present) can be fluidically connected to facilitate delivery of negative pressure to the wound. The system can be configured to automatically detect whether the canister is positioned in the fluid flow path between the negative pressure source and the dressing while negative pressure source provides negative pressure to the wound dressing. Operation of the system can be adjusted
(Continued)

based on whether presence of the canister has been detected. For example, a value of an operational parameter can be set to indicate that the canister is present.

20 Claims, 12 Drawing Sheets

Related U.S. Application Data continuation of application No. PCT/US2016/046903, filed on Aug. 12, 2016.

(60) Provisional application No. 62/204,660, filed on Aug. 13, 2015.

(52) U.S. Cl.
CPC ............ *A61M 1/0023* (2013.01); *A61M 1/60* (2021.05); *A61M 2205/14* (2013.01); *A61M 2205/15* (2013.01); *A61M 2205/3331* (2013.01)

(58) Field of Classification Search
CPC .......... A61M 2205/3331; A61M 1/916; A61M 1/984; A61M 1/985
See application file for complete search history.

(56) References Cited

U.S. PATENT DOCUMENTS

| | | |
|---|---|---|
| 4,731,076 A | 3/1988 | Noon et al. |
| D357,735 S | 4/1995 | McPhee |
| 5,514,088 A | 5/1996 | Zakko |
| 5,712,795 A | 1/1998 | Layman et al. |
| 6,027,490 A | 2/2000 | Radford et al. |
| 6,203,291 B1 | 3/2001 | Stemme et al. |
| 6,232,680 B1 | 5/2001 | Bae et al. |
| 6,396,407 B1 | 5/2002 | Kobayashi |
| D475,132 S | 5/2003 | Randolph |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,214,202 B1 | 5/2007 | Vogel et al. |
| D581,042 S | 11/2008 | Randolph et al. |
| D590,934 S | 4/2009 | Randolph et al. |
| D602,582 S | 10/2009 | Pidgeon et al. |
| D602,583 S | 10/2009 | Pidgeon et al. |
| D602,584 S | 10/2009 | Pidgeon et al. |
| 7,611,500 B1 | 11/2009 | Lina et al. |
| D625,801 S | 10/2010 | Pidgeon et al. |
| 7,857,806 B2 | 12/2010 | Karpowicz et al. |
| D630,313 S | 1/2011 | Pidgeon et al. |
| D630,725 S | 1/2011 | Pidgeon et al. |
| 7,927,319 B2 | 4/2011 | Lawhorn |
| D645,137 S | 9/2011 | Gonzalez |
| 8,021,348 B2 | 9/2011 | Risk, Jr. et al. |
| 8,062,272 B2 | 11/2011 | Weston |
| 8,066,243 B2 | 11/2011 | Svedman et al. |
| 8,070,735 B2 | 12/2011 | Koch et al. |
| D654,164 S | 2/2012 | Cole et al. |
| D660,409 S | 5/2012 | Taggerty et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,308,714 B2 | 11/2012 | Weston et al. |
| 8,317,774 B2 | 11/2012 | Adahan |
| 8,366,692 B2 | 2/2013 | Weston |
| 8,409,160 B2 | 4/2013 | Locke et al. |
| 8,480,641 B2 | 7/2013 | Jacobs |
| 8,540,688 B2 | 9/2013 | Eckstein et al. |
| 8,641,693 B2 | 2/2014 | Locke et al. |
| 8,668,677 B2 | 3/2014 | Eckstein et al. |
| 8,827,967 B2 | 9/2014 | Lawhorn |
| 8,858,517 B2 | 10/2014 | Pan et al. |
| 8,905,985 B2 | 12/2014 | Allen et al. |
| 9,050,398 B2 | 6/2015 | Armstrong et al. |
| 9,084,845 B2 | 7/2015 | Adie et al. |
| 9,138,531 B2 | 9/2015 | Yodfat et al. |
| 9,199,010 B2 | 12/2015 | Yao et al. |
| D750,222 S | 2/2016 | Chang |
| D750,235 S | 2/2016 | Maurice |
| D750,236 S | 2/2016 | Maurice |
| D757,260 S | 5/2016 | Lombardi, III et al. |
| 9,327,063 B2 | 5/2016 | Locke et al. |
| 9,333,281 B2 | 5/2016 | Giezendanner et al. |
| D764,047 S | 8/2016 | Bjelovuk et al. |
| D764,048 S | 8/2016 | Bjelovuk et al. |
| D764,653 S | 8/2016 | Bjelovuk et al. |
| D764,654 S | 8/2016 | Bjelovuk et al. |
| 9,415,199 B2 | 8/2016 | Tsai |
| 9,427,505 B2 | 8/2016 | Askem et al. |
| D765,830 S | 9/2016 | Bjelovuk et al. |
| 9,445,948 B2 * | 9/2016 | Smola .................... A61M 1/90 |
| D773,658 S | 12/2016 | Bow |
| 9,586,036 B2 | 3/2017 | Masuda et al. |
| D788,293 S | 5/2017 | Eckstein |
| D791,939 S | 7/2017 | Tuturro et al. |
| D792,586 S | 7/2017 | Becker |
| 9,737,649 B2 | 8/2017 | Begin et al. |
| D797,275 S | 9/2017 | Evans et al. |
| D802,744 S | 11/2017 | Bjelovuk et al. |
| 9,901,664 B2 | 2/2018 | Askem |
| D813,374 S | 3/2018 | Bjelovuk et al. |
| D814,016 S | 3/2018 | Bjelovuk et al. |
| D815,726 S | 4/2018 | Bjelovuk et al. |
| D815,727 S | 4/2018 | Bjelovuk et al. |
| D820,980 S | 6/2018 | Maurice |
| 9,923,401 B2 | 10/2018 | Jung |
| 10,124,093 B1 | 11/2018 | Francis et al. |
| 10,143,785 B2 | 12/2018 | Adams et al. |
| 10,155,070 B2 | 12/2018 | Childress et al. |
| D852,356 S | 6/2019 | Steele et al. |
| 2002/0013545 A1 | 1/2002 | Soltanpour et al. |
| 2002/0030002 A1 | 3/2002 | Verkaart et al. |
| 2002/0098097 A1 | 7/2002 | Singh |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2007/0032763 A1 | 2/2007 | Vogel |
| 2008/0200857 A1 * | 8/2008 | Lawhorn ................. G08B 31/00 602/41 |
| 2009/0216205 A1 | 8/2009 | Ryan et al. |
| 2009/0299306 A1 | 12/2009 | Buan |
| 2010/0244780 A1 | 9/2010 | Turner |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0289913 A1 * | 11/2012 | Eckstein .................. A61M 1/73 604/319 |
| 2013/0012772 A1 | 1/2013 | Gunday et al. |
| 2013/0025692 A1 | 1/2013 | Heide et al. |
| 2013/0237937 A1 | 9/2013 | Ramella et al. |
| 2013/0267917 A1 | 10/2013 | Pan et al. |
| 2013/0274718 A1 | 10/2013 | Yao et al. |
| 2014/0023533 A1 | 1/2014 | Ishii et al. |
| 2014/0276488 A1 | 9/2014 | Locke et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 * | 1/2016 | Luckemeyer ......... A61M 3/022 604/315 |
| 2016/0101278 A1 | 4/2016 | Norris et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0303358 A1 | 10/2016 | Croizat et al. |
| 2017/0165405 A1 | 6/2017 | Muser et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0296716 A1 | 10/2017 | Middleton et al. |

(56) References Cited

U.S. PATENT DOCUMENTS

| | | |
|---|---|---|
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0264181 A1 | 9/2018 | Gregory et al. |
| 2018/0308578 A1 | 10/2018 | Armstrong et al. |
| 2018/0318476 A1 | 11/2018 | Askem et al. |
| 2019/0388279 A1 | 12/2019 | Hartwell et al. |
| 2020/0121833 A9 | 4/2020 | Askem et al. |

FOREIGN PATENT DOCUMENTS

| | | |
|---|---|---|
| EP | 2255837 A1 | 12/2010 |
| EP | 3 124 059 | 2/2017 |
| EP | 3 124 060 | 2/2017 |
| FR | 2 939 320 | 6/2010 |
| GB | 1220857 | 1/1971 |
| JP | S56-047279 | 4/1981 |
| JP | H01-101978 | 4/1989 |
| JP | H07-96029 | 4/1995 |
| JP | 2007-218241 | 8/2007 |
| JP | 2010-502405 | 1/2010 |
| JP | 6047279 B2 | 12/2016 |
| WO | WO 1996/05873 | 2/1996 |
| WO | WO 2000/61206 | 10/2000 |
| WO | WO 2003/081762 | 10/2003 |
| WO | WO 2008/033788 | 3/2008 |
| WO | WO 2008/039223 | 4/2008 |
| WO | WO-2009071924 A1 | 6/2009 |
| WO | WO 2011/075706 | 6/2011 |
| WO | WO-2011094410 A2 | 8/2011 |
| WO | WO 2012/004298 | 1/2012 |
| WO | WO 2012/100624 | 8/2012 |
| WO | WO 2013/015827 | 1/2013 |
| WO | WO-2013078214 A1 | 5/2013 |
| WO | WO 2014/115819 | 7/2014 |
| WO | WO 2014/164655 | 10/2014 |
| WO | WO 2015/197462 | 12/2015 |
| WO | WO 2016/018448 | 2/2016 |
| WO | WO 2016/103033 | 6/2016 |
| WO | WO 2016/103035 | 6/2016 |
| WO | WO 2016/109048 | 7/2016 |
| WO | WO 2017/027850 | 2/2017 |
| WO | WO 2017/160412 | 9/2017 |
| WO | WO 2018/009873 | 1/2018 |
| WO | WO 2018/009880 | 1/2018 |

OTHER PUBLICATIONS

International Search Report and Written Opinion, re PCT Application No. PCT/US2016/046903, dated Nov. 7, 2016.
International Preliminary Reporton Patentability, re PCT Application No. PCT/US2016/046903, dated Feb. 22, 2018.

* cited by examiner

SYSTEMS AND METHODS FOR APPLYING REDUCED PRESSURE THERAPY

CROSS-REFERENCE TO RELATED APPLICATIONS

This application is a continuation of U.S. patent application Ser. No. 15/895,953, filed on Feb. 13, 2018, which is a continuation of International Application No. PCT/US2016/046903, filed on Aug. 12, 2016, which published in English as WO 2017/027850 A1 on Feb. 16, 2017, and which claims the benefit of U.S. Provisional Patent Application No. 62/204,660, filed Aug. 13, 2015; the disclosure of each which applications is hereby incorporated by reference in its entirety.

BACKGROUND

Embodiments or arrangements disclosed herein relate to methods and apparatuses for dressing and treating a wound with topical negative pressure (TNP) therapy. For example, but without limitation, any embodiments disclosed herein relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system or assembly for providing negative pressure to a wound site. Wound treatment apparatuses may also comprise wound dressings that may be used in combination with the pump assemblies described herein, and connectors for connecting the wound dressings to the pump assemblies.

In some embodiments, an apparatus for applying negative pressure to a wound is disclosed. The apparatus includes a negative pressure source and a controller. The negative pressure source provides, via a fluid flow path including at least one lumen, negative pressure under a dressing placed over a wound. The controller detects whether a canister is positioned in the fluid flow path between the negative pressure source and the dressing, the canister being configured to store fluid removed from the wound. In response to detecting that the canister is positioned in the fluid flow path, the controller sets a value of a parameter to a first value indicating that the canister is positioned in the fluid flow path. In response to detecting that the canister is not positioned in the fluid flow path, the controller sets the value of the parameter to a second value indicating that the canister is not positioned in the fluid flow path.

The apparatus of the preceding paragraph can further include one or more of the following features: The controller can detect whether the canister is positioned in the fluid flow path based at least on a level of activity of the negative pressure source and a first change in negative pressure provided by the negative pressure source to the dressing. The controller can detect whether the canister is positioned in the fluid flow path while the negative pressure source is maintaining negative pressure under the dressing within a negative pressure range. The first change in negative pressure can be one of (i) an average change in negative pressure between a maximum overshoot pressure and an upper hysteresis point pressure over a first time period while the negative pressure source is maintaining negative pressure under the dressing within the negative pressure range or (ii) an average change in negative pressure between the upper hysteresis point pressure and a lower hysteresis point pressure over a second time period while the negative pressure source is maintaining negative pressure under the dressing within the negative pressure range. The lower hysteresis point can be pressure measured at a time when the negative pressure source is activated to restore pressure under the dressing to be within the negative pressure range; the upper hysteresis point pressure can be pressure measured at a time when the negative pressure source is deactivated after pressure under the dressing is restored to be within the negative pressure range; and the maximum overshoot pressure can be a maximum negative pressure measured after the negative pressure source is deactivated and before the negative pressure is reactivated. The controller can further detect whether the canister is positioned in the fluid flow path based at least on a second change in negative pressure provided by the negative pressure source to the dressing, the second change in negative pressure being different from the first change in negative pressure. The controller can further determine the level of activity of the negative pressure source based at least on a duty cycle of the negative pressure source. The controller can further determine the first change in negative pressure from a pressure measured at a pump head of the negative pressure source. The controller can detect whether the canister is positioned in the fluid flow path without determining a pressure under the dressing and a flow rate of fluid in the fluid flow path. The controller can detect whether the canister is positioned in the fluid flow path without using a direct measurement of an operating speed of the negative pressure source. The controller can further: when the value of the parameter is set to the first value, activate an alarm based at least on a comparison between the level of activity of the negative pressure source and a first activity threshold; and when the value of the parameter is set to the second value, activate the alarm based at least on a comparison between the level of activity of the negative pressure source and a second activity threshold different from the first activity threshold. The alarm can be indicative of a blockage in the fluid flow path. The alarm can be indicative of a leak in the fluid flow path. The controller can further: when the value of the parameter is set to the first value, clear the alarm based at least on a comparison between the level of activity of the negative pressure source and a third activity threshold; and when the value of the parameter is set to the second value, clear the alarm based at least on a comparison between the level of activity of the negative pressure source and a fourth activity threshold different from the third activity threshold. The controller can further: detect that the canister is not positioned in the fluid flow path in response to determining that a plurality of conditions are satisfied, and detect that the canister is positioned in the fluid flow path in response to determining that at least one of the plurality of conditions is not satisfied. The plurality of conditions can include a first condition indicating whether a level of activity of the negative pressure source meets an activity threshold while the negative pressure source is maintaining negative pressure under the dressing within a negative pressure range. The plurality of conditions can include a second condition indicating whether a first change in negative pressure provided by the negative pressure source to the dressing meets a first pressure threshold while the negative pressure source is maintaining negative pressure under the dressing within the negative pressure range. The plurality of conditions can include a third condition indicating whether a second change in negative pressure provided by the negative pressure source to the dressing does not meet a second pressure threshold while the negative pressure source is maintaining negative pressure under the dressing within the negative pressure range. The first change in negative pressure can include an average change in negative pressure between a maximum overshoot pressure and an upper hysteresis point pressure over a first time period while the negative pressure source is maintaining negative pressure under the dressing within the negative pressure range, and the second change in negative pressure can include an average change in negative pressure between the upper hysteresis point pressure and a lower hysteresis point pressure over a second time period while the negative pressure source is maintaining negative pressure under the dressing within the negative pressure range. The lower hysteresis point can be pressure measured at a time when the negative pressure source is activated to restore pressure under the dressing to be within the negative pressure range; the upper hysteresis point pressure can be pressure measured at a time when the negative pressure source is deactivated after pressure under the dressing is restored to be within the negative pressure range; and the maximum overshoot pressure can be a maximum negative pressure measured after the negative pressure source is deactivated and before the negative pressure source is reactivated. The apparatus can further include a switch configured to toggle according to a user input, and the controller can detect whether the canister is positioned in the fluid flow path based at least on a position of the switch. The apparatus can further include a sensor configured to output an indication of whether the canister is positioned in the fluid flow path, and the controller can detect whether the canister is positioned in the fluid flow path based at least on the indication. The sensor can include a proximity sensor. The sensor can include a pressure sensor. The pressure sensor can output the indication when tabs used to secure the canister to a housing are engaged, and the negative pressure source can be disposed in the housing. The controller can operate the negative pressure source to provide negative pressure under the dressing. The apparatus can further include the dressing.

In some embodiments, a method of operating the apparatus of any of the preceding two paragraphs is disclosed.

In some embodiments, a method for operating a negative pressure wound therapy apparatus is disclosed. The method includes: providing negative pressure with a negative pressure source, via a fluid flow path including at least one lumen, under a dressing placed over a wound; detecting whether a canister is positioned in the fluid flow path between the negative pressure source and the dressing, the canister being configured to store fluid removed from the wound; in response to detecting that the canister is positioned in the fluid flow path, setting a value of a parameter to a first value indicating that the canister is positioned in the fluid flow path; in response to detecting that the canister is not positioned in the fluid flow path, setting the value of the parameter to a second value indicating that the canister is not positioned in the fluid flow path; and modifying operation of the negative pressure wound therapy apparatus based at least on whether the value of the parameter is the first value or the second value.

The method of the preceding paragraph can further include one or more of the following features: The detecting can be performed while performing the providing. The detecting can be performed while maintaining negative pressure under the dressing below a negative pressure threshold with the negative pressure source. When negative pressure under the dressing is below the negative pressure threshold, the negative pressure source can be performing negative pressure therapy. The method can further include: when the value of the parameter is set to the first value, the modifying operation of the negative pressure wound therapy apparatus can include activating an alarm based at least on a comparison between a level of activity of the negative pressure source and a first activity threshold; and when the value of the parameter is set to the second value, the modifying operation of the negative pressure wound therapy apparatus can include activating the alarm based at least on a comparison between the level of activity of the negative pressure source and a second activity threshold different from the first activity threshold. The alarm can be indicative of a blockage in the fluid flow path. The alarm can be indicative of a leak in the fluid flow path. The method can further include: when the value of the parameter is set to the first value, the modifying operation of the negative pressure wound therapy apparatus can include operating the negative pressure source in a first mode of operation; and when the value of the parameter is set to the second value, the modifying operation of the negative pressure wound therapy apparatus can include operating the negative pressure source in a second mode of operation different from the first mode of operation.

In some embodiments, a method for operating a negative pressure wound therapy apparatus is disclosed. The method includes: detecting whether a negative pressure source is coupled via a first or second fluid flow path to a dressing placed over a wound, the first fluid flow path including at least one lumen and not comprising a canister configured to store fluid removed from the wound, the second fluid flow path including at least one lumen and the canister; in response to detecting that the negative pressure source is coupled via the first fluid flow path, selecting a first mode of operation and providing negative pressure with the negative pressure source via the first fluid flow path to the dressing in accordance with the first mode of operation; and in response to detecting that the negative pressure source is coupled via the second fluid flow path, selecting a second mode of operation different from the first mode of operation and providing negative pressure with the negative pressure source via the second fluid flow path to the dressing in accordance with the second mode of operation.

The method of the preceding paragraph can further include the following feature: A first dressing can be coupled to the first fluid flow path and a second dressing different from the first dressing can be coupled to the second fluid flow path.

In some embodiments, an apparatus for applying negative pressure to a wound is disclosed. The apparatus includes (i) a negative pressure source disposed in a housing and (ii) a controller. The negative pressure source is configured to be coupled, via a fluid flow path, to a dressing placed over a wound and to provide negative pressure to the dressing. The fluid flow path includes at least one lumen. The controller is configured to, while the negative pressure source provides negative pressure to the dressing, detect whether a canister is positioned in the fluid flow path between the negative pressure source and the dressing. The canister is configured to store fluid removed from the wound. In addition, the controller is configured to: (i) in response to detecting that the canister is positioned in the fluid flow path, set a value of a parameter to a first value indicating that the canister is positioned in the fluid flow path, and (ii) in response to detecting that the canister is not positioned in the fluid flow path, set the value of the parameter to a second value indicating that the canister is not positioned in the fluid flow path.

The apparatus of the preceding paragraph can further include one or more of the following features: The controller can detect whether the canister is positioned in the fluid flow path based at least on a level of activity of the negative pressure source and a first change in negative pressure provided by the negative pressure source to the dressing. The controller can detect whether the canister is positioned in the fluid flow path while the negative pressure source is maintaining negative pressure under the dressing within a negative pressure range. The first change in negative pressure can include one of (i) an average change in negative pressure between a maximum overshoot pressure and an upper hysteresis point pressure over a first time period while the negative pressure source is maintaining negative pressure under the dressing within the negative pressure range or (ii) an average change in negative pressure between the upper hysteresis point pressure and a lower hysteresis point pressure over a second time period while the negative pressure source is maintaining negative pressure under the dressing within the negative pressure range. The lower hysteresis point can be pressure measured at a time when the negative pressure source is activated to restore pressure under the dressing to be within the negative pressure range. The upper hysteresis point pressure can be pressure measured at a time when the negative pressure source is deactivated after pressure under the dressing is restored to be within the negative pressure range. The maximum overshoot pressure can be a maximum negative pressure measured after the negative pressure source is deactivated and before the negative pressure source is reactivated. The controller can detect whether the canister is positioned in the fluid flow path based at least on a second change in negative pressure provided by the negative pressure source to the dressing, the second change in negative pressure being different from the first change in negative pressure. The controller can measure a duty cycle of the negative pressure source and determine the level of activity of the negative pressure source based at least on the duty cycle of the negative pressure source. The controller can determine the first change in negative pressure from a pressure measured at a pump head of the negative pressure source. The controller can detect whether the canister is positioned in the fluid flow path without determining a pressure under the dressing and a flow rate of fluid in the fluid flow path. The controller can detect whether the canister is positioned in the fluid flow path without using a direct measurement of an operating speed of the negative pressure source. The controller can: (i) when the value of the parameter is set to the first value, activate an alarm based at least on a comparison between the level of activity of the negative pressure source and a first activity threshold, and (ii) when the value of the parameter is set to the second value, activate the alarm based at least on a comparison between the level of activity of the negative pressure source and a second activity threshold different from the first activity threshold. The alarm can be indicative of a blockage in the fluid flow path. The alarm can be indicative of a leak in the fluid flow path. The controller can: (i) when the value of the parameter is set to the first value, clear the alarm based at least on a comparison between the level of activity of the negative pressure source and a third activity threshold, and (ii) when the value of the parameter is set to the second value, clear the alarm based at least on a comparison between the level of activity of the negative pressure source and a fourth activity threshold different from the third activity threshold. The controller can: (i) detect that the canister is not positioned in the fluid flow path in response to determining that a plurality of conditions are satisfied, and (ii) detect that the canister is positioned in the fluid flow path in response to determining that at least one of the plurality of conditions is not satisfied. The plurality of conditions can include a first condition indicating whether a level of activity of the negative pressure source meets an activity threshold while the negative pressure source is maintaining negative pressure under the dressing within a negative pressure range. The plurality of conditions can include a second condition indicating whether a first change in negative pressure provided by the negative pressure source to the dressing meets a first pressure threshold while the negative pressure source is maintaining negative pressure under the dressing within the negative pressure range. The plurality of conditions can include a third condition indicating whether a second change in negative pressure provided by the negative pressure source to the dressing does not meet a second pressure threshold while the negative pressure source is maintaining negative pressure under the dressing within the negative pressure range. The first change in negative pressure can be an average change in negative pressure between a maximum overshoot pressure and an upper hysteresis point pressure over a first time period while the negative pressure source is maintaining negative pressure under the dressing within the negative pressure range, and the second change in negative pressure comprises an average change in negative pressure between the upper hysteresis point pressure and a lower hysteresis point pressure over a second time period while the negative pressure source is maintaining negative pressure under the dressing within the negative pressure range. The apparatus can include the dressing.

In some embodiments, a method of operating the apparatus of any of the preceding two paragraphs is disclosed.

In some embodiments, a method for operating a negative pressure wound therapy apparatus is disclosed. The method includes: providing negative pressure with a negative pressure source, via a fluid flow path, to a dressing placed over a wound, the fluid flow path comprising at least one lumen; while providing negative pressure to the dressing, detecting whether a canister is positioned in the fluid flow path between the negative pressure source and the dressing, the canister configured to store fluid removed from the wound; in response to detecting that the canister is positioned in the fluid flow path, setting a value of a parameter to a first value indicating that the canister is positioned in the fluid flow path; in response to detecting that the canister is not positioned in the fluid flow path, setting the value of the parameter to a second value indicating that the canister is not positioned in the fluid flow path; and modifying operation of the negative pressure wound therapy apparatus based at least on setting the value of the parameter to the first or second value.

The method of the preceding paragraph can further include one or more of the following features: The method can include (i) when the value of the parameter is set to the first value, activating an alarm based at least on a comparison between the level of activity of the negative pressure source and a first activity threshold, and (ii) when the value of the parameter is set to the second value, activating the alarm based at least on a comparison between the level of activity of the negative pressure source and a second activity threshold different from the first activity threshold. The alarm can be indicative of a blockage in the fluid flow path. The alarm can be indicative of a leak in the fluid flow path. The method can include (i) when the value of the parameter is set to the first value, operating the negative pressure source in a first mode of operation, and (ii) when the value of the parameter is set to the second value, operating the negative pressure source in a second mode of operation different from the first mode of operation.

In some embodiments, a method of operating a negative pressure wound therapy apparatus is disclosed. The method includes: detecting whether a negative pressure source is coupled via a first or second fluid flow path to a dressing placed over a wound, the first fluid flow path comprising at least one lumen and not comprising a canister configured to store fluid removed from the wound, and the second fluid flow path comprising at least one lumen and the canister; in response to detecting that the negative pressure source is coupled via the first fluid flow path, selecting a first mode of operation and providing negative pressure with the negative pressure source via the first fluid flow path to the dressing in accordance with the first mode of operation; and in response to detecting that the negative pressure source is coupled via the second fluid flow path, selecting a second mode of operation different from the first mode of operation and providing negative pressure with the negative pressure source, via the second fluid flow path, to the dressing in accordance with the second mode of operation.

The method of the preceding paragraph can further include the following feature: A first dressing can be coupled to the first fluid flow path and a second dressing different from the first dressing can be coupled to the second fluid flow path.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which.

DETAILED DESCRIPTION

Overview

Embodiments disclosed herein relate to systems and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is farther from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
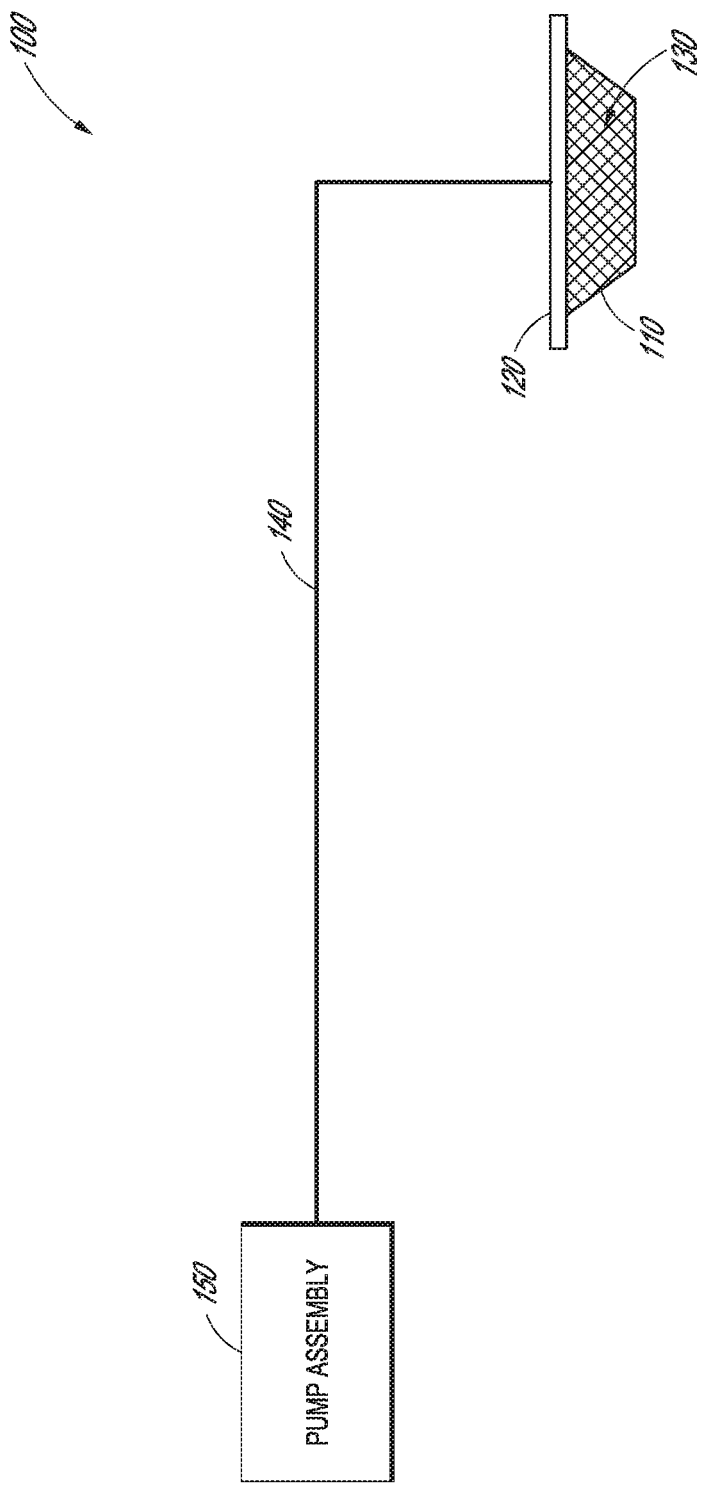
FIG. 1 illustrates a reduced pressure wound therapy system including a pump assembly according to some embodiments.

FIG. 1 illustrates an embodiment of a negative or reduced pressure wound treatment (or TNP) system 100 comprising a wound filler 130 placed inside a wound cavity 110, the wound cavity 100 sealed by a wound cover 120. The wound filler 130 in combination with the wound cover 120 can be referred to as wound dressing. A single or multi lumen tube or conduit 140 connects the wound cover 120 with a pump assembly 150 configured to supply reduced pressure. The wound cover 120 can be in fluidic communication with the wound cavity 110. In any of the system embodiments disclosed herein, the pump assembly can be a canisterless pump assembly (meaning that exudate is collected in the wound dressing or is transferred via conduit 140 for collection to another location). However, any of the pump assembly embodiments disclosed herein can be configured to include or support a canister. Additionally, in any of the system embodiments disclosed herein, any of the pump assembly embodiments can be mounted to or supported by the wound dressing, or adjacent to the wound dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as of the pump assembly 150. The pump assembly 150 can be miniaturized and portable, although larger conventional pumps can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and the wound cover 120 or wound filler 130 can include superabsorbing material to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate as well as to wounds that exude larger amount of wound exudate.

Some embodiments of the system are designed to operate without the use of an exudate canister. Some embodiments can be configured to support an exudate canister. In some embodiments, configuring the pump assembly 150 and conduit 140 so that the conduit 140 can be quickly and easily removed from the pump assembly 150 can facilitate or improve the process of wound dressing or pump changes, if necessary. Any of the pump embodiments disclosed herein can be configured to have any suitable connection between the tubing and the pump. In some embodiments, the pump assembly 150 can further detect whether an exudate canister may be in use and accordingly operate in a canisterless mode of operation or a canister mode of operation.

In some embodiments, the pump assembly 150 can be configured to deliver negative pressure of approximately −80 mmHg, or between about −20 mmHg and −200 mmHg. As explained herein, these pressures may be relative to normal ambient atmospheric pressure thus, −200 mmHg would be about 560 mmHg in practical terms. The pressure range can be between about −40 mmHg and −150 mmHg. Alternatively, a pressure range of up to −75 mmHg, up to −80 mmHg or over −80 mmHg can be used. Also, a pressure range of below −75 mmHg can be used. Alternatively, a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister (not shown). The canister can, for example, store more than 50 mL of fluid, such as 100 mL to 1000 mL of fluid, 300 mL to 800 mL of fluid, or 500 mL of fluid in some implementations. In some embodiments, fluid is absorbed by the wound filler 130 or one or more absorbent layers (not shown) and canister is not utilized.

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly

Figure 2A:
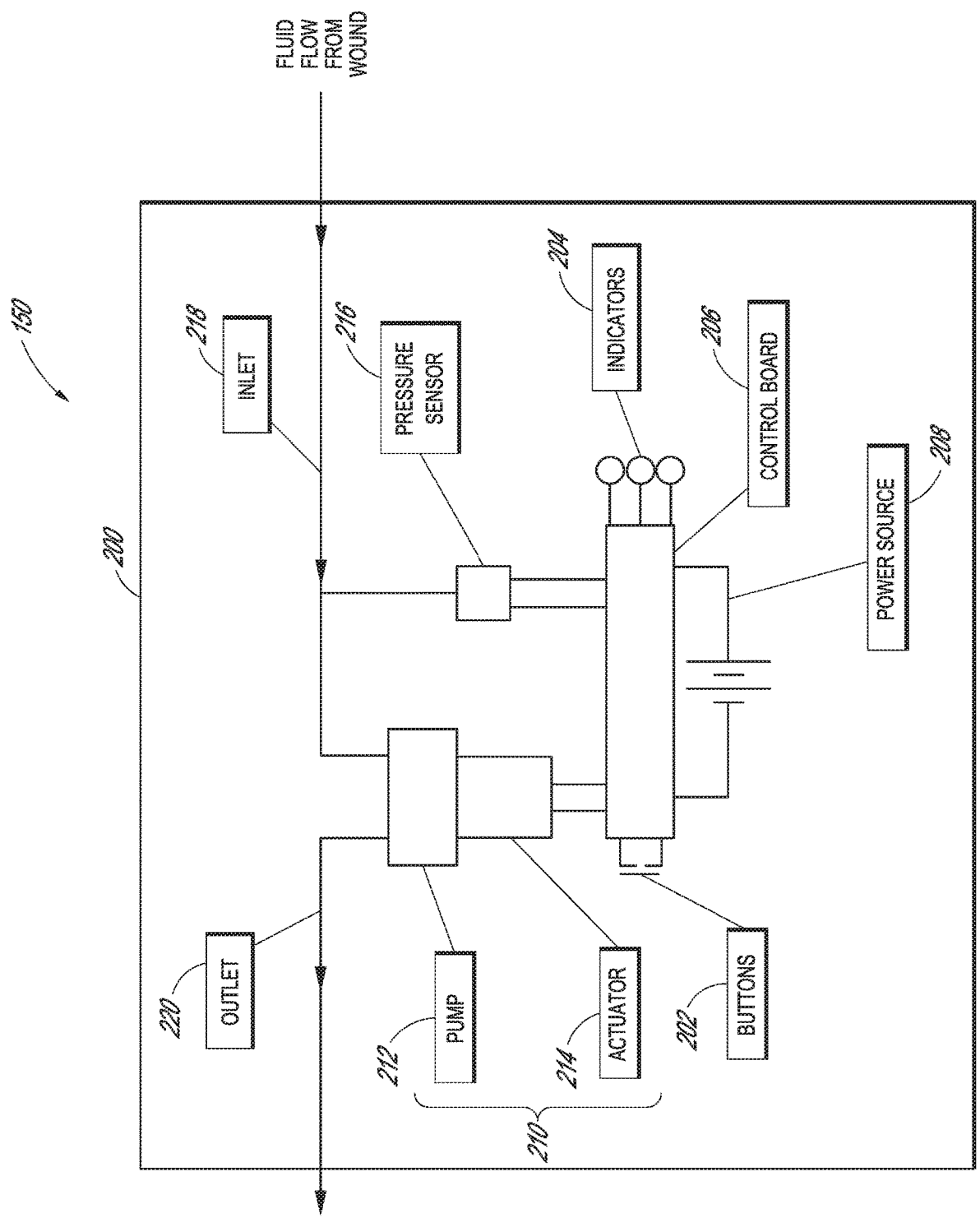
FIGS. 2A and 2B illustrate schematics of the pump assembly of FIG. 1 according to some embodiments.

FIG. 2A illustrates a schematic of the pump assembly 150 according to some embodiments. The pump assembly 150 can include a housing 200 that encloses or supports at least some components of the pump assembly 150. The pump assembly 150 can include one or more switches or buttons 202, one or more indicators 204, and a control board 206. The one or more buttons 202 and the one or more indicators 204 can be in electrical communication with the control board 206. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

The one or more indicators 204 can indicate one or more operating or failure conditions of the pump assembly 150. Each of the one or more indicators 204 may provide an indication regarding a different operating or failure condition. In some implementations, an active (e.g., lit) indicator of the one or more indicators 204 can represent a certain operation condition for the pump assembly 150. For example, a dressing indicator of the one or more indicators 204 can provide an indication as to presence of leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a battery indicator of the one or more indicators 204 can provide an indication as to remaining capacity or life of a power source, such as batteries, and an active battery indicator can represent a low capacity. In some embodiments, the one or more indicators 204 can represent a combination of one or more of the above operating or failure conditions of the pump assembly 150 or other operating or failure conditions for the pump assembly 150.

In some implementations, the one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. In various implementations, one or more buttons indicators 204 can be included on a touchscreen interface.

The pump assembly 150 can be powered by a power source 208 such as a battery power cell or any other suitable power source. The pump assembly 150 can also include a source of negative pressure 210, which can include a pump 212 powered by an actuator 214 such as an electric motor. In some embodiments, the actuator 214 is integrated into the pump 212. The pump assembly 150 can also include one or more pressure sensors 216.

The pump assembly 150 can further include an inlet 218 to connect the pump assembly 150 to the wound dressing. For example, the inlet 218 can be a connector for connecting the inlet 218 to a conduit which is in fluid communication with the wound dressing via a fluid flow path.

The pump assembly 150 can also be connected to an outlet 220. The outlet 220 can vent or exhaust gas to the atmosphere. In some embodiments, a filter (not shown) can be interposed between the outlet and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet and the atmosphere. The dampening component can reduce the noise generated by the pump assembly 150 during operation.

In some embodiments, the pump assembly 150 can include a valve (not shown), such as a one-way valve, in a flow passage between the wound dressing and the inlet 218. The valve can help maintain a level of negative pressure when the pump assembly 150 is not active. In addition, the valve can help avoid leaks. The valve can also help prevent fluids or exudate aspirated or removed from the wound from entering the pump assembly 150.

Figure 2B:
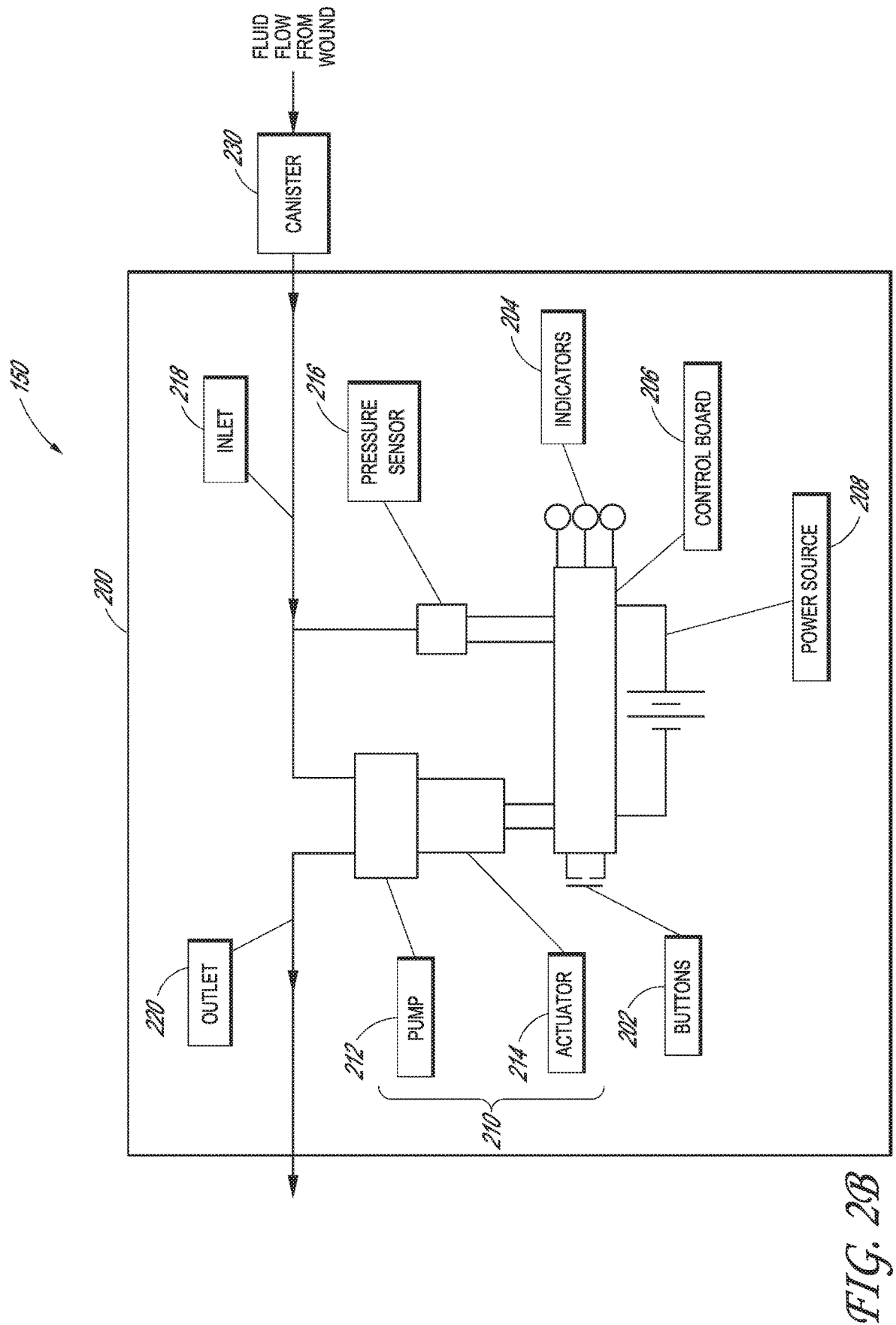

FIG. 2B illustrates a schematic of the pump assembly 150 according to some embodiments. The pump assembly 150 illustrated in FIG. 2B can be the same as the pump assembly 150 illustrated in FIG. 2A with the exception of a canister 230 additionally positioned in the fluid flow path between the inlet 218 and the wound dressing. The canister 230 can be part of the pump assembly 150 and can be mounted to or near the housing 200. For example, the canister 230 can be removably attached to the housing 200. In other implantations, the canister 230 can be separate from the pump assembly 150 yet be positioned in the fluid flow path between the inlet 218 and the wound dressing. The canister 230 can store fluid from the wound dressing, such as exudate removed from the wound. The canister 230 can be optionally included and removed from the flow path so that the pump assembly 150 can be used in either a canister mode of operation or canisterless mode of operation. When the pump assembly 150 operates in the canister mode of operation, the control board 206 can control one or more operations of the pump assembly 150 differently from when the pump assembly 150 operates in the canisterless mode of operation. For example, the control board 206 can vary one or more parameters controlling the delivery of negative pressure supplied to the wound dressing and vary one or more conditions for activating the one or more indicators 204 based at least on whether the pump assembly 150 operates in the canister mode of operation or the canisterless mode of operation.

Figure 2C:
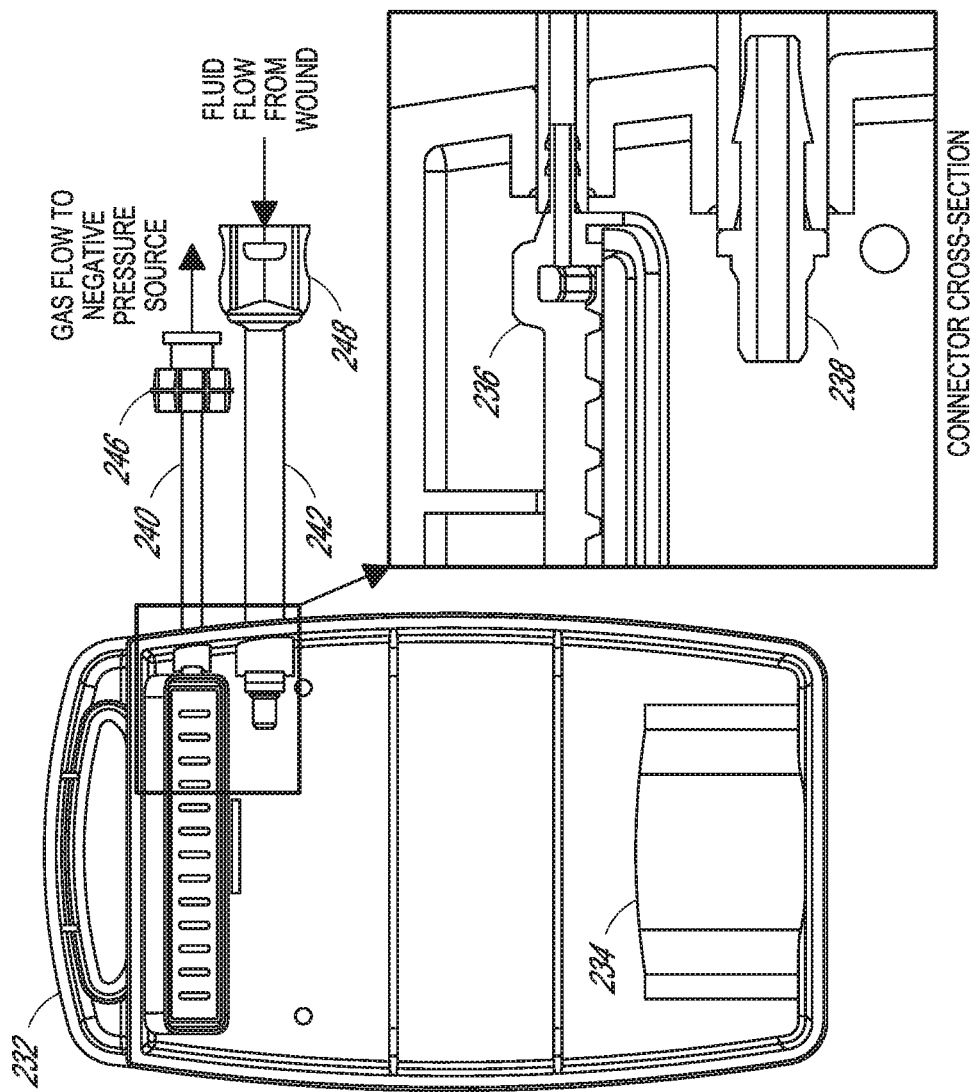
FIG. 2C illustrates the canister of FIG. 2B according to some embodiments.

FIG. 2C illustrates the canister 230 according to some embodiments. The canister 230 can be constructed of two canister parts that are combined together, such as by hot plate welding, to form a canister housing 232. The canister 230 can include a pouch 234, such as a Super Absorbing Powder (SAP) Pouch, within the canister housing 232 that can mitigate fluid from sloshing around within the canister housing 232. The pouch 234 can burst once wetted with fluid and, if a SAP Pouch, may release SAP crystals. The canister 230 can also include a pump connector 236 and a wound dressing connector 238 for coupling the canister housing 232 respectively to the housing 200 and the wound dressing. The pump connector 236 can be coupled to a first tubing 240 that extends outside of the canister housing 232, and the wound dressing connector 238 can be coupled to a second tubing 242 that extends outside of the canister housing 232. The first tubing 240 and pump connector 236 can be further connected to a filter (not shown) inside the canister housing 232. The filter can be a hydrophobic filter that allows gas to pass but blocks exudate from the wound dressing, such as an expanded polytetrafluoroethylene (ePTFE) by Gore™. The filter may or may not include a carbon filter or blocking filter layers in some implementations. As illustrated, the first tubing 240 can be a shorter length of tubing and have a thinner internal diameter than the second tubing 242 in some embodiments.

The connection and seal between the pump connector 236 and the first conduit or tubing 240 and the connection and seal between the wound dressing connector 238 and the second conduit or tubing 242 can be made without use of glue. For example, prior to combining the two parts of the canister housing 232, the first tubing 240 can be passed through the pump connector 236 and coupled to a barb fitting, and the second tubing 242 can be passed through the wound dressing connector 238 and coupled to another barb fitting. The first tubing 240, the second tubing 242, and the barbs can then be pulled back into the canister housing 232. The first tubing 240 can be compressed between the barbs and the pump connector 236, and the second tubing 242 can be compressed between the other barbs and the wound dressing connector 238. These connections and seals can couple the first tubing 240 and the second tubing 242 to the canister housing 232 and prevent the first tubing 240 and the second tubing 242 from being pulled out of the canister housing 232. In some implementations, glue or another adhesive can further be used to enhance the seal between connections and seals. Other suitable connectors can be used instead of or in addition to barbs. The wound dressing connector 238 can be a check valve, such as a duck-bill check valve, to prevent fluid or other materials from the canister housing 232 from entering the wound dressing connector 238 and flowing back under the wound dressing.

The first tubing 240 and the second tubing 242 can include connectors for coupling to tubings that are respectively connected to the negative pressure source and the wound dressing. For example, the first tubing 240 can include a first mounting connector 246, which is illustrated as a "screw-on" connector, and the second tubing 242 can include a second mounting connector 248, which is illustrated as a "snap-on" (such as quick release) connector. Other suitable connectors, however, can be used.

Figure 3:
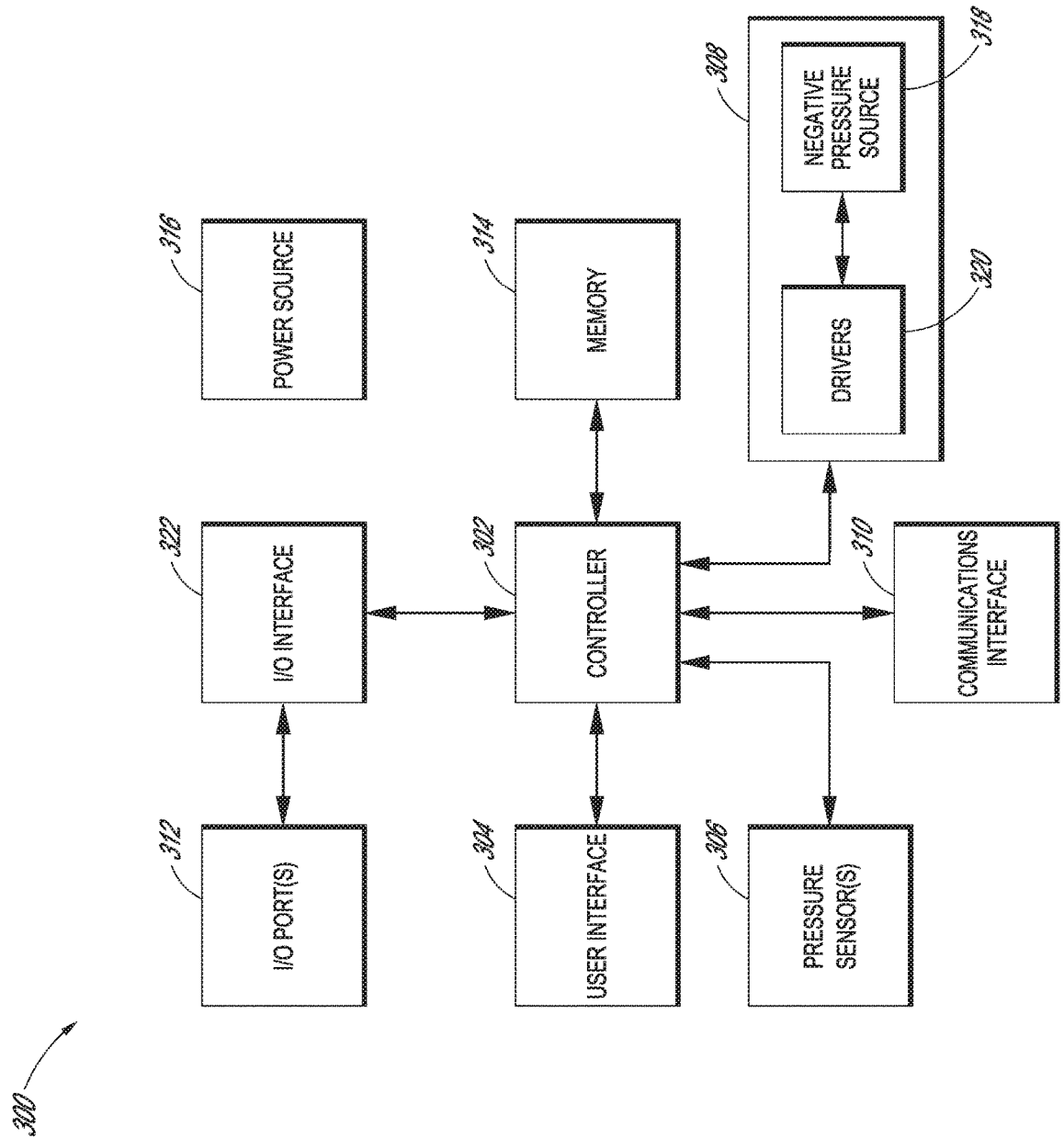
FIG. 3 illustrates a block diagram of electrical components of the pump assembly of FIG. 1 according to some embodiments.

FIG. 3 illustrates a block diagram of electrical components 300 of the pump assembly 150 according to some embodiments. The electrical components 300 can operate to accept user input, provide output to the user, operate the pump system and the source of negative pressure, provide network connectivity, and so on. The electrical components 300 can be mounted on one or more PCBs (not shown), such as the control board 206. The electrical components 300 can include a controller 302 that may be part of the control board 206, for instance. The controller 302 can be a general purpose processor, such as a low-power processor or an application specific processor. The controller 302 can be configured as a "central" processor in the electronic architecture of the pump assembly 150, and the controller 302 can coordinate the activity of one or more other controllers, such as one or more controllers of the user interface 304, I/O interface 322, negative pressure control module 308, communications interface 310, and the like.

The electrical components 300 can include the user interface 304 which may include one or more components for accepting user input and providing indications to users, such as buttons, indicators (e.g., LEDs), displays, etc. The user interface 304 can include the one or more buttons 202 and the one or more indicators 204. Inputs to the pump assembly 150 and outputs from the pump assembly 150 can controlled via one or more input/output (I/O) ports 312 controlled by the I/O interface 322. For example, the I/O interface 322 can receive data from the one or more I/O ports 312, such as serial, parallel, hybrid ports, expansion ports, and the like. The I/O ports 312 can include, for instance, one or more of USB ports, SD ports, Compact Disc (CD) drives, DVD drives, FireWire ports, Thunderbolt ports, PCI Express ports, and the like. The controller 302, along with one or more other controllers, can store data in a memory 314, which can be internal or external to the pump assembly 150. Any suitable type of memory can be used, including volatile or non-volatile memory, such as RAM, ROM, WORM, magnetic memory, solid-state memory, MRAM, and the like or any combination thereof. The electrical components 300 can be powered by a power source 316, which can include one or more disposable or rechargeable batteries, power from mains, or the like. The power source 316 can be internal or external to the pump assembly 150.

The negative pressure control module 308 can be the same as or part of the source of negative pressure 210 and control the operation of a negative pressure source 318. The negative pressure source 318 can be a diaphragm pump, for example. Other suitable pumps for the negative pressure source 318 can include peristaltic pumps, rotary pumps, rotary vane pumps, scroll pumps, screw pumps, liquid ring pumps, piezoelectric pumps (such as diaphragm pumps operated by a piezoelectric transducer), voice coil pumps, and the like. The negative pressure control module can include a driver 320 configured to control the operation of the negative pressure source 318. For example, the driver 320 can provide power to the negative pressure source 318. Power can be provided in a form of a voltage or current signal. The driver 320 can control the negative pressure source 318 using pulse-width modulation (PWM). A control signal for driving the negative pressure source 318 (sometimes referred to as a pump drive signal) can be a 0-100% duty cycle PWM signal. In other implementations, the driver 320 can control the negative pressure source 318 using any other suitable control, such as proportional-integral-derivative (PID). In some embodiments, the driver 320 may not be present, and the controller 302 can control the operation of the negative pressure source 318.

The controller 302 can receive information from one or more sensors, such as one or more pressure sensors 306, placed in a suitable location like in a fluid flow path, such as a pressure monitor placed within an intake manifold of the pump assembly 150. The one or more pressure sensors 306 can include the pressure sensor 216. The controller 302 can measure pressure in the fluid flow path, using data received from the one or more pressure sensors 306, calculate the rate of fluid flow, and control the negative pressure source 318 so that desired level of negative pressure is achieved in the wound cavity 110 or under the wound dressing. The desired level of negative pressure can be pressure set or selected by a user. Pressure measured by the one or more pressure sensors 306 can be provided to the controller 302 so that the controller 302 can determine and adjust the pump drive signal to achieve the desired negative pressure level. The tasks associated with controlling the negative pressure source 318 can be offloaded to one or more other controllers of the negative pressure control module 308 in some instances.

In any embodiments, it may be advantageous to utilize multiple processors for performing various tasks. For example, a first processor can be responsible for user activity, and a second processor can be responsible for controlling the negative pressure source 318. This way, the activity of controlling the negative pressure source 318, which may necessitate a higher level of responsiveness, can be offloaded to a dedicated processor and, thereby, may not be interrupted by user interface tasks, which may take longer to complete because of interactions with the user.

The communications interface 310 can provide wired or wireless connectivity. The communications interface 310 can utilize one or more antennas (not shown) for sending and receiving data. The communications processor 310 can, for example, provide one or more of the following types of connections: Global Positioning System (GPS) technology, cellular or other connectivity, such as 2G, 3G, LTE, 4G, WiFi, Internet connectivity, Bluetooth, zigbee, RFID, and the like. Additionally, any embodiments disclosed herein can be configured to synchronize, upload, or download data to or from the pump assembly 150 to or from a portable data device, such as a tablet, smart phone, or other similar devices.

Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications interface 310 can provide dual GPS/cellular functionality. Cellular functionality can, for example, be 3G or 4G functionality. In such cases, if the GPS module is not be able to establish satellite connection due to various factors including atmospheric conditions, building or terrain interference, satellite geometry, and so on, the device location can be determined using the 3G or 4G network connection, such as by using cell identification, triangulation, forward link timing, and the like. The communications interface 310 can further include a SIM card, and SIM-based positional information can be obtained.

Pump System Control

Figure 4:
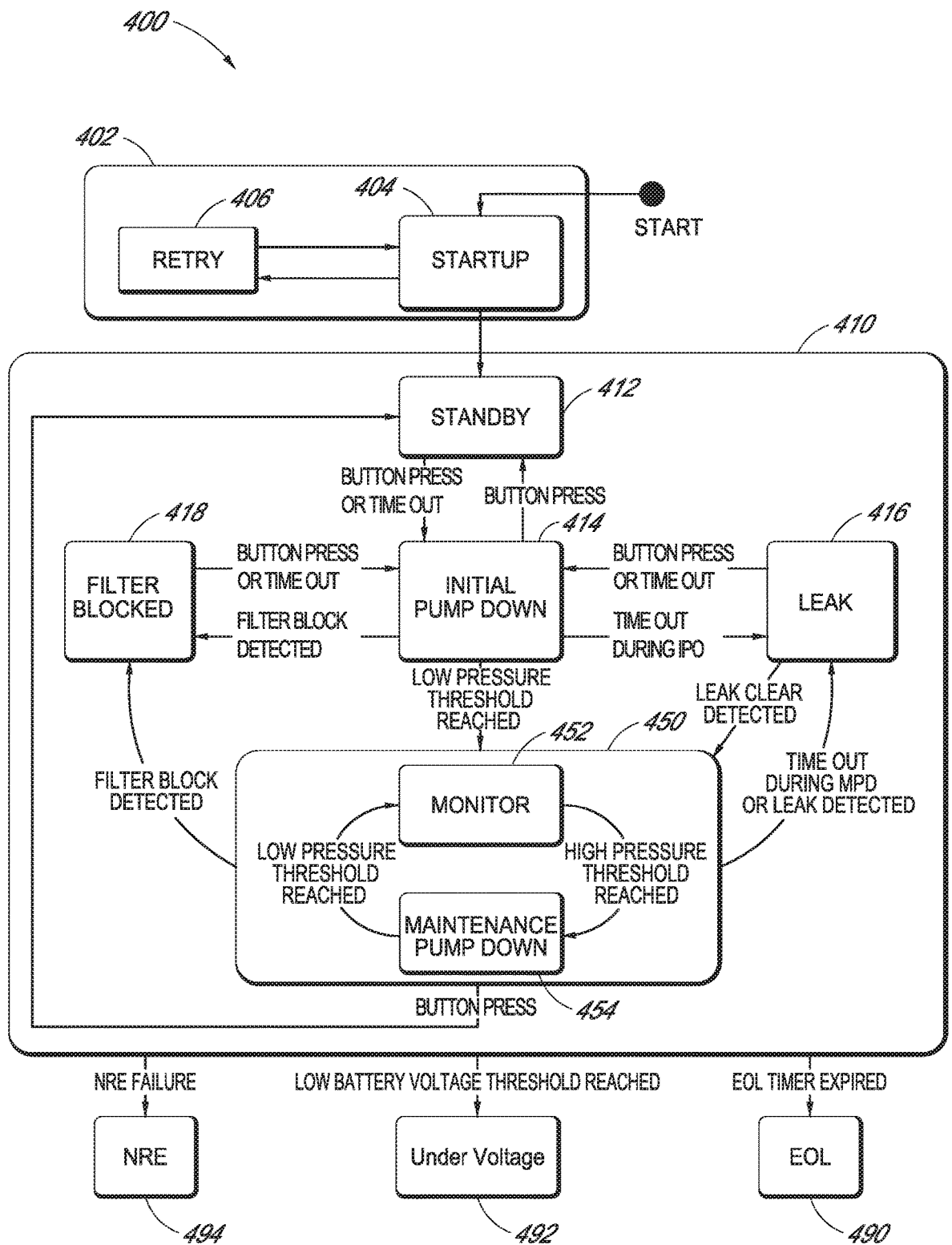
FIG. 4 is a state diagram showing operation of the pump assembly of FIG. 1 according to some embodiments.

FIG. 4 is a state diagram 400 showing operation of the pump assembly 150 according to some embodiments. For example, the pump assembly 150 using the approaches of the state diagram 400 can provide a suitable balance between uninterrupted delivery of therapy or avoidance of inconveniencing the user by, for example, frequently or needlessly pausing or suspending therapy and a desire to conserve power, limit noise and vibration generated by the source of negative pressure 210. The controller 302 or the control board 206 can implement the flow of the state diagram 400. As is illustrated in FIG. 4, the operation of the pump assembly 150 can, in some implementations, be grouped into three general modes: initialization mode 402, operational mode 410, which includes maintenance mode 450, and end of life mode 490. As is illustrated in FIG. 4, initialization mode 402, operational mode 410, which includes maintenance mode 450, can each include multiple states or transitions between states.

In some embodiments, so long as a power source is not connected or removed, or the pump assembly 150 has not been activated (e.g., by pulling an activation strip, triggering the switch, or the like), the pump assembly 150 can remain in an inactive state. While remaining in this state, the pump assembly 150 can remain inactive. When the power source is connected or the pump assembly 150 has been activated from the inactive state, such as being activated for the first time, the pump assembly 150 can transition to the initialization mode 402, where power on self-test(s) (POST) and other tests can be performed as shown in startup 404. Power on self-test(s) can include performing various checks to ensure proper functionality of the system, such as testing one or more components of the system including, but not limited to, memory such as the memory 314 (e.g., performing a check, such as a cyclic redundancy check, of the program code to determine its integrity, testing the random access memory, etc.), reading a pressure sensor such as the pressure sensor 216 or the one or more pressure sensors 306, to determine whether the pressure values are within suitable limits, reading the remaining capacity or life of the power source (e.g., battery voltage, current, etc.) like the power source 208 or the power source 316 to determine whether it is within suitable limits, testing the source of negative pressure 210. In some embodiments, one or more of the one or more indicators 204 can indicate to the user (e.g., by blinking or flashing once) that the pump assembly 150 is undergoing POST test(s). In some embodiments, during the initialization mode 402, all indicators can continuously remain on.

In some embodiments, if one or more of the POST test(s) fail, the pump assembly 150 can transition to a retry state 406. The retry state 406 can be include a delay or require user input before retrying the POST test(s). In some embodiments, if one or more of POST test(s) fail after one or more retries, the pump assembly 150 can transition to a non-recoverable error state. While in this state, the pump assembly 150 can deactivate therapy, and indicators can be indicate to the user that an error was encountered. In some embodiments, all indicators can remain active. Based on the severity of error, in some embodiments, the pump assembly 150 can recover from the error and continue operation (or transition to the non-recoverable error state 494). As is illustrated in FIG. 4, the pump assembly 150 can transition to the non-recoverable error state 494 upon encountering a fatal error during operation. Fatal errors can include program memory errors, program code errors (e.g., encountering an invalid variable value), controller operation errors (e.g., watchdog timer expires without being reset by the controller such as the controller 302), component failure (e.g., inoperative source of negative pressure, inoperative pressure sensor, etc.), and any combination thereof.

When initialization has been successfully completed in startup 404, the pump assembly 150 can transition to the operational mode 410. This transition can be indicated to the user by deactivating or activating one or more indicators. In some embodiments, when the pump assembly 150 transitions into the operational mode 410, the pump assembly 150 can first enter a standby state 412 in which the pump assembly 150 may be paused. While the pump assembly 150 remains in the standby state 412, the user can be provided an indication, such as by deactivating or deactivating indicators (e.g., an OK indicator or a dressing indicator). In some embodiments, the user can be provided an indication of the standby state 412 by deactivating all indicators. In some embodiments, therapy can be suspended while the pump assembly 150 remains in the standby state 412. For example, the source of negative pressure of the pump assembly 150 can be deactivated (or turned off). In some embodiments, indication can be provided to the user by deactivating the source of negative pressure 210.

In some embodiments, the pump assembly 150 can make a transition from the standby state 412 to an initial pump down ("IPD") state 414 (where the pump assembly 150 is configured to deliver therapy) in response to receiving a signal from the user. For example, the user can press a button to start, suspend, and/or restart therapy. In some embodiments, the pump assembly 150 can monitor the duration of time the pump assembly 150 remains in the standby state 412. This can be accomplished, for example, by maintaining a timer (in firmware, software, hardware or any combination thereof), which can be reset and started when the pump assembly 150 transitions into the standby state 412. The pump assembly 150 can automatically make the transition from the standby state 412 to the IPD state 414 when the time duration meets, such as becomes equal to or exceeds, a threshold (e.g., times out). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly 150 nears the end of life, the threshold can be decreased used over the lifespan of the pump assembly 150. This can advantageously ensure that the battery is more efficiently over the lifespan of the pump assembly 150 by reducing the amount of time spent in the standby state 412 and utilizing more of the battery by activating the source of negative pressure 210 sooner. In some embodiments, the pump assembly 150 can monitor the entire amount of time spent in the standby state 412 and store this information in memory.

During the IPD state 414, the pump assembly 150 can activate the source of negative pressure 210 to begin therapy and reduce pressure in the TNP system 100 or some portion thereof, such as the fluid flow path between the source of negative pressure 210 and the wound dressing. In some embodiments, the pump assembly 150 can reduce pressure in the TNP system 100 to a desired pressure, such as a low pressure threshold. The pump assembly 150 can intermittently or continuously monitor the pressure in the TNP system 100 or some portion thereof. For example, the pump assembly 150 can monitor the pressure in the TNP system 100 or some portion thereof at a preset sampling rate of approximately 100 ms. In some embodiments, the sampling rate can be between approximately 20 ms and approximately 500 ms, between approximately 50 ms and 250 ms, between approximately 80 ms and 150 ms, approximately 100 ms, any value or subrange with these ranges, or any other sampling rate as desired. In some embodiments, the pump assembly 150 can also calculate the rate of pressure change to estimate the amount of time until the pump assembly 150 reaches a desired pressure, such as the low pressure threshold.

In some embodiments, the user can pause therapy by activating the switch (e.g., pressing the button), thereby causing the pump assembly 150 to make a transition from the IPD state 414 to the standby state 412. In some embodiments, the pump assembly 150 can be configured so that the user can only pause therapy, whereas disconnecting the power source (e.g., removing batteries) stops therapy. As such, in some embodiments, the pump assembly 150 can potentially time-out while in the standby state 412 and resume operation thereby reducing any energy expended while in the standby state 412. After being paused by the user, the pump assembly 150 can transition from the standby state 412 to the IPD state 414 upon receiving a user input such as a button press. In some embodiments, after being paused by the user, the pump assembly 150 can automatically make the transition from the standby state 414 to the IPD state 414 when the time duration meets a threshold. The threshold can be the same or different than the threshold of the standby state 414 described above when the pump assembly 150 enters the standby state 414 after startup 404.

When the pump assembly 150 transitions into and remains in the standby state 412, the user can be provided an indication. For example, in some embodiments, all indicators can be deactivated. In some embodiments, the pump assembly 150 can deactivate an indicator (e.g., an OK indicator) and cause another indicator (e.g., a dressing indicator) to flash or blink. In some embodiments, therapy can be suspended while the pump assembly 150 remains in the standby state 412. For example, the source of negative pressure 210 can be deactivated (or turned off), which provides the indication to the user that the pump assembly 150 is in the standby state 412.

The pump assembly 150 can transition from the IPD state 414 into a leak state 416 when a number of retry cycles exceeds a retry limit or when a duty cycle of the pump is determined to exceed a duty cycle limit. Exceeding a retry limit or duty cycle limit can, in some instances, reflect the presence of a leak in the TNP system 100. The retry limit or duty cycle limit can vary, in some implementations, according to whether the pump assembly 150 is operating in the canister mode of operation or the canisterless mode of operation. In some embodiments, the pump assembly 150 can further transition from the IPD state 414 to the leak state 416 when a threshold pressure is not reached within a desired amount of time. The inability for the threshold pressure to reach the threshold pressure within a desired amount of time can reflect the presence of a leak in the TNP system 100. In some embodiments, an indicator (e.g., a leak indicator or dressing indicator) can blink or flash intermittently or continuously to indicate to the user the presence of a leak in the TNP system 100. Upon transition to the leak state 414, the source of negative pressure 210 can be deactivated. Alternatively, the source of negative pressure 210 can remain active.

After entering the leak state 416, the pump assembly 150 can transition from the leak state 416 to the IPD state 414 upon receiving a user input such as a button press. This can advantageously give the user some time to mitigate or remove the leak, such as by checking the connections to the wound dressing or checking the seal of the wound dressing around the wound. In some embodiments, the pump assembly 150 can monitor the duration of time the pump assembly 150 remains in the leak state 416. This can be accomplished, for example, by maintaining a timer (in firmware, software, hardware or any combination thereof), which can be reset and started when the pump assembly 150 transitions into the leak state 416. In some embodiments, after entering the leak state 416, the pump assembly 150 can automatically make the transition from the leak state 416 to the IPD state 414 when the time duration meets a threshold. The threshold can be the same or different than the other time thresholds described herein, such as that of the standby state 412 to the IPD state 414. The threshold can be the same or different depending on the state or mode prior to transitioning to the leak state 416 (e.g., the IPD state 414 or the maintenance mode 450). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly 150 nears the end of life, the threshold can be decreased provided the battery has sufficient capacity remaining. This can advantageously ensure that the battery is more efficiently used over the lifespan of the pump assembly 150 by reducing the amount of time spent in the leak state 416 and utilizing more of the battery by activating the source of negative pressure 210 sooner. The pump assembly 150 can transition into other modes or states, such as the maintenance mode 450, after activating the switch or automatically after meeting the threshold. In some embodiments, the pump assembly 150 can transition to the IPD state 414 or the maintenance mode 450 depending on operating conditions, such as the pressure at the time of the transition. The threshold used for determining whether to transition from the leak state 416 to the maintenance mode 450 can vary according to whether the pump assembly 150 is operating in the canister mode of operation or the canisterless mode of operation.

As noted above, in some embodiments, the pump assembly 150 can operate without a canister and the wound dressing can retain exudate aspirated from the wound. Such dressing can include a filter, such as a hydrophobic filter, that prevents passage of liquids downstream of the dressing (toward the pump assembly 150). In other embodiments, the pump assembly 150 can operate with a canister for storing at least part of exudate aspirated from the wound. Such a canister can include a filter, such as a hydrophobic filter, that can prevent passage of liquids downstream of the dressing (toward the pump assembly 150). In yet other embodiments, both the dressing and the canister can include filters that prevent passage of liquids downstream of the dressing and the canister.

The pump assembly 150 can transition from the IPD state 414 into a filter blocked state 418 when the pump assembly 150 determines that a filter, such as a wound dressing filter, has encountered a blockage (e.g., caused by the wound dressing being filled with exudate to capacity or nearly to capacity or caused by fluid or solid build up in the flow path). In some embodiments, an indicator (e.g., a filter blocked indicator) can blink or flash intermittently or continuously to indicate to the user the presence of a blockage. In some embodiments, the transition to the filter blocked state 418 can be made when a canister filter is blocked. The pump assembly 150 can transition from the IPD state 414 into a leak state 416 when a number of retry cycles exceeds a retry limit or when a duty cycle of the pump is determined to exceed a duty cycle limit. Exceeding a retry limit or duty cycle limit can, in some instances, reflect the presence of a blockage in the TNP system 100. The retry limit or duty cycle limit can vary, in some implementations, according to whether the pump assembly 150 is operating in the canister mode of operation or the canisterless mode of operation.

After entering the filter blocked state 418, the pump assembly 150 can transition from the filter blocked state 418 to the IPD state 414 upon receiving a user input such as a button press. This can advantageously give the user an opportunity to mitigate or remove the blockage, such as by changing the wound dressing or the canister. In some embodiments, the pump assembly 150 can monitor the duration of time the pump system remains in the filter blocked state 418. This can be accomplished, for example, by maintaining a timer (in firmware, software, hardware or any combination thereof), which can be reset and started when the pump assembly 150 transitions into the filter blocked state 418. In some embodiments, after entering the filter blocked state 418, the pump assembly 150 can automatically make the transition from the filter blocked state 418 to the IPD state 414 when the time duration meets a threshold. The threshold can be the same or different than the other time thresholds described herein, such as that of the standby state 412 to the IPD state 414 or the leak state 416 to the IPD state 414. The threshold can be the same or different depending on the state or mode prior to transitioning to the filter blocked state 418 (e.g., the IPD state 414 or the maintenance mode 450). In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly 150 nears the end of life (as is explained below), the threshold can be decreased provided the battery has sufficient capacity remaining. This can advantageously ensure that the battery is more efficiently used over the lifespan of the pump assembly 150 by reducing the amount of time spent in the filter blocked state 416 and utilizing more of the battery by activating the source of negative pressure 210 sooner. The pump assembly 150 can transition into other modes or states, such as the maintenance mode 450, after activating the switch or automatically after meeting the threshold. In some embodiments, the pump system can transition to the IPD state 414 or the maintenance mode 450 depending on operating conditions, such as the pressure at the time of the transition.

During the IPD state 414, once the pump assembly 150 has detected that the pressure within the pump assembly 150 or some portion thereof, such as the fluid flow path between the source of negative pressure 210 and the wound dressing, is at or around the low pressure threshold, the pump assembly 150 can transition into the maintenance mode 450 and, in particular, to the monitor state 452. For example, the low pressure threshold can be approximately −90 mmHg. In some embodiments, the low pressure threshold can be between approximately −50 mmHg and approximately −250 mmHg, between approximately −75 mmHg and approximately −125 mmHg, between approximately −80 mmHg and −115 mmHg, approximately −94 mmHg, any value or subrange within these ranges, or any other value as desired.

During the maintenance mode 450, the pump assembly 150 can advantageously monitor and maintain the pressure within the TNP system 100 or some portion thereof, such as the fluid flow path between the source of negative pressure and the wound dressing, within a target pressure range (or operating range). For example, in some embodiments, during the maintenance mode 450, the pump assembly 150 can maintain the pressure at the source negative pressure 210 between a high pressure threshold and a low pressure threshold. For example, the high pressure threshold can be approximately −70 mmHg. In some embodiments, the high pressure threshold can be between approximately −40 mmHg and approximately −200 mmHg, between approximately −60 mmHg and approximately −100 mmHg, between approximately −70 mmHg and −80 mmHg, approximately −71 mmHg, approximately −67 mmHg, any value or subrange within these ranges, or any other value as desired. The low pressure threshold can be approximately −90 mmHg. In some embodiments, the low pressure threshold during the maintenance mode 450 can be the same as the low pressure threshold during the IPD state 414. In some embodiments, the low pressure threshold during the maintenance mode 450 can be different from the low pressure threshold during the IPD state 414. As shown in the illustrated embodiment, the maintenance mode 450 can include a monitor state 452 and a maintenance pump down ("MPD") state 454.

During the monitor state 452, the pump assembly 150 can monitor the pressure in the pump assembly 150 or some portion thereof, such as a fluid flow path between the source of negative pressure 210 and the wound dressing, to ensure that the pressure within the pump assembly 150 or the monitored portion thereof is maintained between a high pressure threshold and a low pressure threshold. The source of negative pressure can be deactivated during the monitor state 452. The pump assembly 150 can intermittently or continuously monitor the pressure in one or more positions in the TNP system 100, such as at or near a pump head of the source of negative pressure, at or near the inlet, at or near the wound dressing, or at or near one or more suitable locations in the TNP system. The pump assembly 150 can, for example, monitor the pressure at a preset sampling rate of approximately 1 second. In some embodiments, the sampling rate can be between approximately 50 ms and approximately 5 seconds, between approximately 200 ms and 2 seconds, between approximately 500 ms and 2 seconds, approximately 1 second, any value or subrange with these ranges, or any other sampling rate as desired. In some embodiments, the sampling rate during the monitor state 452 can be less than the sampling rate during the IPD state 414 to advantageously reduce power usage and extend the life of the power source. A lower sampling rate can be used, in some embodiments, as the rate of pressure change during the monitor state 452 (e.g., when the source of negative pressure is deactivated) can be less than the rate of pressure change when the source of negative pressure is activated. In some embodiments, the pump assembly 150 can also calculate the rate of pressure change to estimate the amount of time until the pump assembly 150 reaches a desired pressure, such as a low pressure threshold.

The pump assembly 150 can stay in the monitor state 452 until the pump assembly 150 detects that the pressure in the TNP system 100 or some portion thereof, such as a fluid flow path between the source of negative pressure 210 and the wound dressing, is at or around a high pressure threshold. Upon detecting that the TNP system 100 or some portion thereof is at or around the high pressure threshold, the pump assembly 150 can transition to the MPD state 454. During the MPD state 454, the pump assembly 150 can activate the source of negative pressure to begin therapy and reduce pressure in the TNP system 100 or some portion thereof until the pressure is at or near the low pressure threshold. In some embodiments, the low pressure threshold can be the same or similar to the low pressure threshold discussed in connection with the IPD state 414. In some embodiments, the low pressure threshold can be different from that in the IPD state 414.

The pump assembly 150 can continually monitor the pressure at a preset sampling rate. In some embodiments, the sampling rate can be the same or similar to the low pressure threshold discussed in connection with the IPD state 414. In some embodiments, the sampling rate can be different from the sampling rate during the IPD state 414. In some embodiments, the pump assembly 150 can also calculate the rate of pressure change to estimate the amount of time until the pump assembly 150 reaches a desired pressure, such as the low pressure threshold. When the pump assembly 150 detects that the pressure in the TNP system 100 or some portion thereof is at or around the low pressure threshold, the pump assembly 150 can transition back to the monitor state 452.

The user can pause therapy by activating the switch (e.g., pressing the button), thereby causing the pump assembly 150 to make a transition from the maintenance mode 450 to the standby state 412. After being paused by the user, the pump assembly 150 can transition from the standby state 412 to the IPD state 414 upon receiving a user input such as a button press. In some embodiments, after being paused by the user, the pump assembly 150 can automatically make the transition from the standby state 412 to the IPD state 414 when the time duration meets a threshold. The threshold can be the same or different than the thresholds discussed above, such as the threshold when the pump assembly 150 enters the standby state 412 from the IPD state 414 from a button press. In some embodiments, such threshold can be a preset value, such as between 1 minute or less and 1 hour or more. In some embodiments, the threshold can be set or changed by the user. In some embodiments, the threshold can be varied based on various operating conditions or on any combination thereof. For example, as the pump assembly 150 nears the end of life (as is explained below), the threshold can be decreased provided the battery has sufficient capacity remaining. In some embodiments, the pump assembly 150 can transition into the maintenance mode 450 after activating the switch or automatically after exceeding the threshold. In some embodiments, the pump assembly 150 can transition to the IPD state 414 or the maintenance mode 450 depending on operating conditions, such as the pressure at the time of the transition.

When the pump assembly 150 transitions into and remains in the standby state 412, the user can be provided an indication. For example, in some embodiments, all indicators can be deactivated. In some embodiments, the pump assembly 150 can deactivate an indicator (e.g., an OK indicator) and cause another indicator (e.g., a dressing indicator) to flash or blink. In some embodiments, therapy can be suspended while the pump assembly 150 remains in the standby state 412. For example, the source of negative pressure can be deactivated (or turned off), which provides the indication to the user that the pump assembly 150 is in the standby state 412.

In some embodiments, the pump assembly 150 can be configured to provide therapy for a predetermined period of time, such as approximately 1 day, 2-10 days, up to 30 days, etc. following a first activation. In some embodiments, such period of time can be a preset value, changed by the user, or varied based on various operating conditions or on any combination thereof. The pump assembly 150 can be disposed upon the expiration of such period of time. Once the pump assembly 150 has been activated, the pump assembly 150 can monitor the duration it has remained active. In some embodiments, the pump assembly 150 can monitor the cumulative duration the pump assembly 150 has remained active. This can be accomplished, for example, by maintaining a timer (in firmware, software, hardware or any combination thereof), that reflects such duration.

When the duration reaches or meets a threshold (e.g., 10 days), the pump system can transition to an end of life (EOL) state 490. The pump assembly 150 can deactivate therapy while remaining in state 490 and indicate to the user that the end of the pump assembly 150 usable life has been reached. For example, the pump assembly 150 can deactivate all indicators or deactivate one or more control buttons. In some embodiments, when the pump system is disposable, transitioning to the end of life state 490 means that the pump assembly 150 can be disposed of. The pump assembly 150 can disable reactivation of the pump assembly 150 once the end of life has been reached. For example, the pump assembly 150 can be configured to not allow reactivation even if the power source is disconnected and reconnected later, which can be accomplished by storing an indication, value, flag, etc. in the read-only memory.

Figure 5:
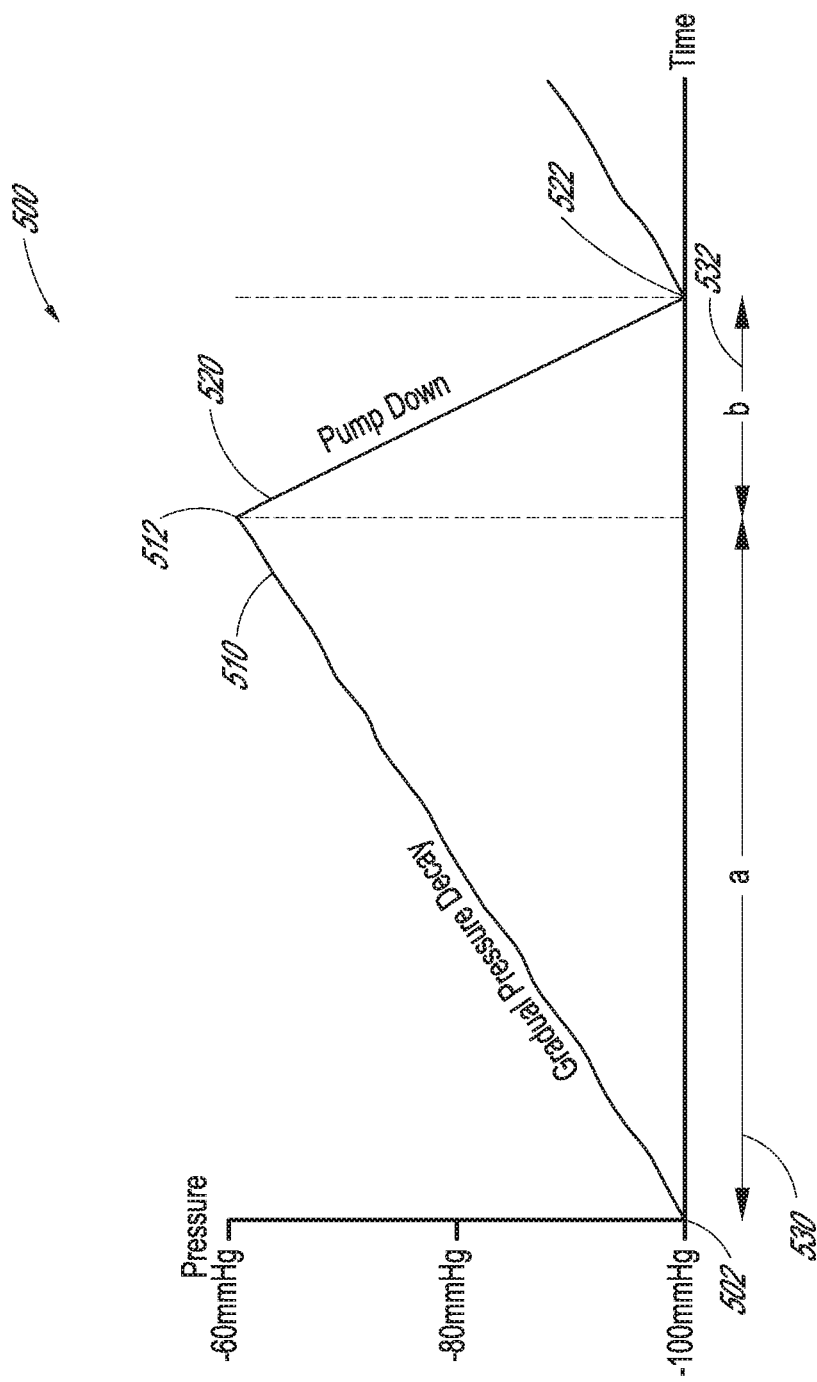
FIG. 5 is a pressure versus time graph depicting operation of the pump assembly of FIG. 1 according to some embodiments.

FIG. 5 is a pressure versus time graph depicting operation of the pump assembly 150 when the source of negative pressure 210 is active, such as during the maintenance mode 450, according to some embodiments. As illustrated by line 510, the pump assembly 150 can enter the monitor state 452 upon detecting that the pressure in the TNP system 100 or some portion thereof, such as a fluid flow path between the source of negative pressure 210 and the wound dressing, is at or near a low pressure threshold 502. In the illustrated embodiment, the low pressure threshold can be approximately −100 mmHg although other low pressure thresholds can be chosen. During the monitor state 452, the pressure may begin to gradually decay due to the source of negative pressure being deactivated and the existence of minor leakages in the TNP system 100. As is illustrated, the pump assembly 150 can monitor pressure over the period of time a, as represented by interval 530.

When the pump assembly 150 detects that the pressure is at or near the high pressure threshold 512, the pump assembly 150 can switch to the MPD state 454 and reactivate the source of negative pressure to lower the pressure as illustrated by line 520. In the illustrated embodiment, the high pressure threshold can be approximately −60 mmHg although other high pressure thresholds can be chosen. As is illustrated, the pump assembly 150 can activate the over the period of time b, as represented by interval 532. When the pump assembly 150 detects that the pressure is at or near the low pressure threshold 522, the pump assembly 150 can switch back to the monitor state 452 and deactivate the source of negative pressure. This process can be repeated as desired. In certain implementations, this process can be performed during the initial pump down 414.

In some embodiments, the duty cycle (DC) of the source of negative pressure 210 over the period illustrated between intervals 510 and 520 (i.e., a+b) can be expressed, on percent scale, as:

$$DC=100\%*[b/(a+b)].$$

Additional details of pump assembly control are disclosed in U.S. Pat. No. 8,734,425, titled "PRESSURE CONTROL APPARATUS," and U.S. Pat. No. 8,905,985, titled "SYSTEMS AND METHODS FOR CONTROLLING OPERATION OF A REDUCED PRESSURE THERAPY SYSTEM," which are incorporated by reference in their entireties as if made part of this disclosure.

In some embodiments, sampling of the pressure can be synchronized with the drive signal. For example, sampling of the pressure within the TNP system 100 or some portion thereof, such as the fluid flow path between the source of negative pressure and the wound dressing, can be performed when the drive signal is approximately at an amplitude that is substantially at an offset or at a zero value. Movement of the source of negative pressure can influence pressure within the pump assembly 150, such as a manifold of the pump assembly 150. By synchronizing sampling of the pressure with the offset or zero value of the drive signal, measurement errors due to pressure fluctuations caused by operation of the motor can be reduced. In some embodiments, sampling of the pressure can be synchronized with the local maxima or local minima of the drive signal. In some embodiments, sampling of the pressure can be synchronized with certain portions of the drive signal, such as portions of the drive signal with a negative rate of change or a positive rate of change.

In some embodiments, the pressure can be sampled one or more times at or around the one or more selected sampling amplitudes such as the offset or zero value, local maxima, or local minima. This can beneficially reduce the likelihood of sampling errors and compensate for the delay elapsed between detection of the one or more selected sampling amplitudes and sampling of the pressure. For example, in some embodiments, the pump assembly 150 can take 8 consecutive samples at approximately each offset or zero value. Accordingly, the pump assembly 150 can take 16 samples over a single period of the drive signal. In some embodiments, the pump assembly 150 can average some or all of the samples taken over a period.

Canister Detection Process

Figure 6:
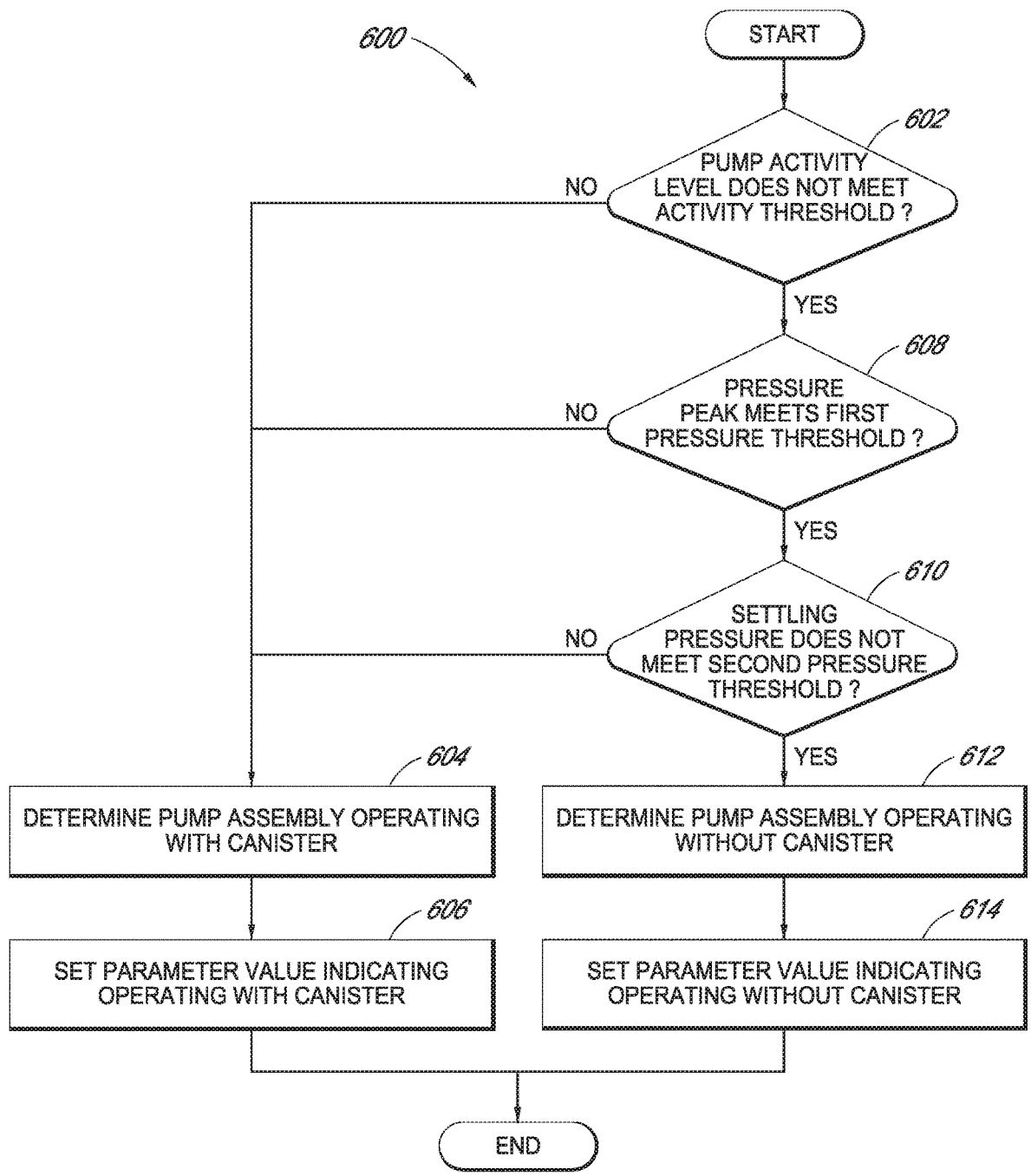
FIG. 6 illustrates a canister detection process performable by the pump assembly of FIG. 1 according to some embodiments.

FIG. 6 illustrates a canister detection process 600 performable by a device, such as the pump assembly 150, according to some embodiments. For convenience, the canister detection process 600 is described in the context of the TNP system 100, but may instead be implemented in other systems described herein or by other computing systems not shown. The canister detection process 600 can enable automatic detection of the presence of an exudate canister such that the presence of an exudate canister can be detected without a user input indicating exudate canister's presence. For example, the canister detection process 600 can be performed by the controller 302 of the control board 206 to detect whether the canister 230 is positioned in the fluid flow path between the inlet 218 and the wound dressing.

Advantageously, in certain embodiments, the canister detection process 600 enables a device like the pump assembly 150 to be fluidically coupled to and suitable for operation with multiple different types of wound dressing including, for instance, (i) a foam or gauze dressing usable with an exudate canister and (ii) an absorbent dressing usable without an exudate canister. As a result, the pump assembly 150 can be used throughout a patient's healing process. For example, the pump assembly 150 can be first used with the foam or gauze dressing usable with an exudate canister, which may be more commonly utilized early in the treatment of a patient with a deep wound, which produces a lot of excaudate. Then, the pump assembly 150 can later be used with the absorbent dressing usable without an exudate canister, which may be used more commonly utilized later in the treatment of the patient as the amount of exudate produced by the wound is reduced due to the healing.

The canister detection process 600 can be implemented based at least on the understanding that the pump assembly 150 operates in an environment with a leak, including inherent leaks present in the system 100 or introduced into the system 100 via a controlled leak (as explained herein), and that the characteristics of the leak may vary depending on whether the pump assembly 150 is operating with or without the canister 230. For example, when the pump assembly 150 is operating without the canister 230, the absorbent dressing used with the pump assembly 150 may be coupled to the pump assembly 150 with a conduit or lumen having a smaller diameter than a conduit or lumen used with the pump assembly 150 when coupled to the foam or gauze dressing. The smaller diameter conduit or lumen can, for instance, create a pressure differential from the pump assembly 150 to the wound 110, which can equalize or settle once the pump 212 turns off. By detecting the pressure differential, the pump assembly 150 can determine whether the pump assembly 150 is coupled to the absorbent dressing or the foam or gauze dressing and thereby also whether the pump assembly 150 is operating with or without the canister 230. As another example, when the pump assembly 150 is operating with the canister 230, the volume serviced by the pump assembly 150 (for example, for maintaining negative pressure) may be greater because of the presence of the canister 230 and because the foam or gauze dressing used with the canister 230 may typically be used for dressing larger wounds. The pump assembly 150 can detect the larger volume serviced by the pump assembly 150 relative to a smaller volume by, for instance, detecting (i) relatively lower peak pressures during the maintenance mode 450 or (ii) the source of negative pressure operating relatively longer to achieve a desired negative pressure.

At block 602 of the canister detection process 600, the canister detection process 600 can determine whether a pump activity level of the pump assembly 150 does not meet an activity threshold. The pump activity level of the pump assembly 150 can, for example, depend on a level of activity of the source of negative pressure 210 of the pump assembly 150. Because the source of negative pressure 210 may be active (for example, to maintain the level of negative pressure under the dressing) for a longer duration when the pump assembly 150 is operating with the canister 230, the pump activity level not meeting the activity threshold can indicate that the pump assembly 150 is operating without the canister 230.

The canister detection process 600 can, for instance, determine the level of activity of the pump assembly 150 based at least on one or more parameters, including but not limited to (i) a duty cycle of the source of negative pressure 210, (ii) a direct feedback measure of the level of activity of the source of negative pressure 210 from the source of negative pressure (for example, a value of a signal directly output by the source of negative pressure 210 indicative of its level of activity, such a tachometer signal or Hall effect signal from the source of negative pressure 210), and (iii) an indirect feedback measure of the level of activity of the source of negative pressure 210, such as (a) a value of a signal from an activity (for example, motion sensor) separate from the source of negative pressure 210 where the signal is responsive to activity of the source of negative pressure 210 or (b) a value of a signal from a pressure sensor in the TNP system 100, such as the pressure sensor 216 where the signal is responsive to activity of the source of negative pressure 210. The canister detection process 600 can determine the level of activity of the pump assembly 150 using the one or more parameters individually or in combination, such as by using a weighted average calculation.

In some implementations, the canister detection process 600 can determine the level of activity of the pump assembly 150 to be a duration of activity or run-time for the source of negative pressure 210 relative to a duration of time. The canister detection process 600 can, for example, use the one or more parameters determine the duration of run-time over a window of time, such as a duration ranging from 30 seconds or less to 100 minutes or more (for example, about 1 minute, 2 minutes, 5 minutes, 10 minutes, 15 minutes, 50 minutes, etc.). The duration of run-time can be averaged or smoothed over a time period, such as the window of time, in some embodiments. In turn, the activity threshold can be a portion or percentage of the window during which the source of negative pressure 210 is running. For example, the activity threshold can be a threshold window duration ranging from 0.5% or less to 10% or more of the window duration, such as about 1%, 2%, 2.5%, 3%, 5%, etc. of the window duration. As one example, if the window of time is 10 minutes and the threshold window duration is 2.5%, the canister detection process 600 can compare the duration of run-time for the source of negative pressure 210, such as an average duration of run-time, to the activity threshold of 0.25 seconds. The activity threshold can be set at pump assembly manufacture, experimentally determined during pump assembly testing, or configurable by a user, in some implementations.

In response to the canister detection process 600 determining that the pump activity level meets the activity threshold, the canister detection process 600 moves to block 604. At block 604, the canister detection process 600 can determine that the pump assembly 150 is operating with the canister 230. At block 606, the canister detection process 600 can set a value of a parameter indicating that the pump assembly 150 is operating with the canister 230. The parameter can, for example, be a flag stored in the memory 314 that may be subsequently referenced by the canister detection process 600 to determine whether the controller is operating with or without the canister 230. As another example, an indication that the pump assembly 150 is operating with the canister 230 can be provided, such as via the one or more indicators 204. After block 606, the canister detection process 600 can then end.

On the other hand, in response to the canister detection process 600 determining that the pump activity level does not meet the activity threshold, the canister detection process 600 moves to block 608. At block 608, the canister detection process 600 can determine whether a pressure peak in the TNP system 100 meets a first pressure threshold. The pressure peak can be a pressure overshoot in the TNP system 100 that occurs after the source of negative pressure 210 stops providing negative pressure to the wound dressing. Because the source of negative pressure 210 may service a smaller volume when the pump assembly 150 is operating without the canister 230, the source of negative pressure 210 can cause a relatively greater pressure peak in a canisterless system than in a system with the canister 230. The canister detection process 600 can thus detect the relatively greater pressure peak as indicative of the pump assembly 150 is operating without the canister 230.

The canister detection process 600 can determine the pressure peak based at least on one or more signals from one or more pressure sensors that measure pressure in the TNP system 100. The one or more pressure sensors can, for example, measure pressure in the fluid flow path between the pump assembly 150, such as the pressure at or near the pump assembly 150 or the pressure under the wound dressing, and output one or more signals responsive to the measured pressure. In some implementations, the one or more pressure sensors can include a pressure sensor like the pressure sensor 216 that measures pressure at or near the pump assembly 150 inlet, such as at a pump head of the source of negative pressure 210. Determination of the pressure peak can be performed without directly measuring pressure under the wound dressing. The canister detection process 600 can determine the pressure peak using one or more values from the one or more signals individually or in combination, such as by using a weighted average calculation.

In some implementations, the canister detection process 600 can determine the pressure peak to be a pressure difference between (i) a maximum pressure overshoot after the source of negative pressure 210 stops providing pressure (the time when the source of negative pressure 210 stops providing pressure can be sometimes referred to as an upper hysteresis point) and (ii) a pressure measure at or near the time when the source of negative pressure 210 stops providing pressure. The canister detection process 600 can, for instance, use the one or more signals from the one or more pressure sensors to determine the pressure peak from (i) the maximum pressure overshoot at a position in the fluid flow path after the source of negative pressure 210 stops providing pressure and (ii) the pressure at the same position in the fluid flow path when the source of negative pressure 210 stops providing pressure. The pressure difference can be averaged or smoothed over a time period, such as over a window of time ranging from 30 seconds or less to 100 minutes or more (e.g., about 1 minute, 2 minutes, 5 minutes, 10 minutes, 15 minutes, 50 minutes, etc.), in some embodiments.

At block 608, the canister detection process 600 can determine if the pressure peak meets the first pressure threshold, which can be a threshold set at manufacture, experimentally-determined during pump assembly testing, or configurable by a user, in some implementations. The first pressure threshold can be established so that a comparison of the pressure peak and the first pressure threshold indicates whether the pump assembly 150 is likely operating with or without the canister 230. In some embodiments, the first pressure threshold can be a value ranging from 3 mmHg or less to 10 mmHg or more, such as about 3 mmHg, 4 mmHg, 5 mmHg, 6 mmHg, 7 mmHg, 8 mmHg, etc. In one example, the first pressure threshold can be about 6 mmHg such that pressure peak not meeting about 6 mmHg indicates the pump assembly 150 is operating with the canister 230 and pressure difference meeting about 6 mmHg indicates the pump assembly 150 is potentially operating without the canister 230.

In response to the canister detection process 600 determining that the pressure peak does not meet the first pressure threshold, the canister detection process 600 moves to block 604. At block 604, the canister detection process 600 can determine that the pump assembly 150 is operating with the canister 230. As explained herein, at block 606, the canister detection process 600 can set the value of a parameter indicating that the pump assembly 150 is operating with the canister 230, and after block 606, the canister detection process 600 can then end.

On the other hand, in response to the canister detection process 600 determining that the pressure peak meets the first pressure threshold, the canister detection process 600 moves to block 610. At block 610, the canister detection process 600 can determine whether a settling pressure does not meet a second pressure threshold. The settling pressure can be a pressure change in the TNP system 100 that occurs a period of time after the source of negative pressure 210 stops providing negative pressure to the wound dressing. Because the source of negative pressure 210 may service a smaller volume when the pump assembly 150 is operating without the canister 230, a relatively lower pressure change will occur in fluid flow path over the period of time after the source of negative pressure 210 stops providing negative pressure in a canisterless system than in a system with the canister 230. The canister detection process 600 can thus detect the relatively lower pressure change as indicative of the pump assembly 150 operating without the canister 230.

The canister detection process 600 can determine the settling pressure based at least on one or more signals from one or more pressure sensors that measure pressure in the TNP system 100. The one or more pressure sensors used to determine the settling pressure can be the same as the one or more pressure sensors used for determining the peak pressure as described with respect to block 608. In some embodiments, at least some of the one or more pressure sensors used to determine the settling pressure can be different from the one or more pressure sensors used to determine the peak pressure. In some implementations, the one or more pressure sensors used to determine the settling pressure can include a pressure sensor that measures pressure at or near the pump assembly 150 inlet, such as at a pump head of the source of negative pressure 210. Determination of the settling pressure can be performed without directly measuring pressure under the wound dressing or using a direct measurement of pressure under the wound dressing. The canister detection process 600 can determine the settling pressure using one or more values from the one or more signals individually or in combination, such as by using a weighted average calculation.

In some implementations, the canister detection process 600 can determine the settling pressure to be a pressure difference between (i) a pressure at the time when the source of negative pressure 210 stops providing pressure (sometimes referred to as an upper hysteresis point) and (ii) a pressure measure after a passage of a duration of time after the source of negative pressure 210 stops providing pressure. The canister detection process 600 can, for instance, use the one or more signals from the one or more pressure sensors to determine the settling pressure from (i) the pressure at a position in the fluid flow path at the time when the source of negative pressure 210 stops providing pressure and (ii) the pressure at the same position after a passage of a duration of time after the source of negative pressure 210 stops providing pressure. The duration can be a time in the range of 100 ms or less to 2000 ms or more, such as about 100 ms, 200 ms, 250 ms, 300 ms, 500 ms, 1000 ms, etc. The settling pressure can be averaged or smoothed over a time period, such as over a window of time ranging from 30 seconds or less to 100 minutes or more (for example, about 1 minute, 2 minutes, 5 minutes, 10 minutes, 15 minutes, 50 minutes, etc.), in some embodiments.

At block 610, the canister detection process 600 can determine if the settling pressure meets the second pressure threshold, which can be a threshold set at manufacture, experimentally-determined during pump assembly testing, or configurable by a user, in some implementations. The second pressure threshold can be established so that a comparison of the settling pressure and the second pressure threshold indicates whether the pump assembly 150 is likely operating with or without the canister 230. In some embodiments, the second pressure threshold can be a value ranging from 3 mmHg or less to 15 mmHg or more, such as about 5 mmHg, 6 mmHg, 7 mmHg, 8 mmHg, 9 mmHg, 10 mmHg, 11 mmHg, 12 mmHg, etc. The second pressure threshold can be the same as or different from the first pressure threshold. In one example, the second pressure threshold can be about 8 mmHg such that settling pressure meeting about 8 mmHg indicates the pump assembly 150 is operating with the canister 230 and pressure differences not meeting 8 mmHg indicate the pump assembly 150 is likely operating without the canister 230.

In response to the canister detection process 600 determining that the settling pressure meets the second pressure threshold, the canister detection process 600 moves to block 604. At block 604, the canister detection process 600 can determine that the pump assembly 150 is operating with the canister 230. As described herein, at block 606, the canister detection process 600 can set the value of a parameter indicating that the pump assembly 150 is operating with the canister 230, and after block 606, the canister detection process 600 can then end.

On the other hand, in response to the canister detection process 600 determining that the settling pressure does not meet the second pressure threshold, the canister detection process 600 moves to block 612. At block 612, the canister detection process 600 can determine that the pump assembly 150 is operating without the canister 230. At block 614, the canister detection process 600 can set a value of a parameter indicating that the pump assembly 150 is operating without the canister 230. The parameter can, for example, be a flag stored in the memory 314 that may be subsequently referenced by the canister detection process 600 to determine whether the controller is operating with or without the canister 230. The parameter set at blocks 604 and 610 can be the same or different parameters. As another example, an indication that the pump assembly 150 is operating without a canister can be provided, such as via the one or more indicators 204. After block 612, the canister detection process 600 can then end.

The canister detection process 600 can be performed when the pump assembly 150 is in the initialization mode 402 or the operational mode 410. In some implementations, however, the canister detection process 600 can be performed when the pump assembly 150 is in the operational mode 410 but not during the initialization mode 402. In yet other implementations, the canister detection process 600 can be performed when the pump assembly 150 is in the maintenance mode 450 or leak state 416 but not during the initialization mode 402 or the other states of the operational mode 410. In one example, the canister detection process 600 determines whether the pump assembly 150 is operating with or without the canister 230 in as little as, for instance, 5 seconds, 15 seconds, 30 seconds, 1 minute, or 5 minutes after initiation of therapy.

As can be seen from FIG. 6, the canister detection process 600 can depend on three conditions (provided in blocks 602, 608, and 610) for determining whether the pump assembly 150 may be operating with or without the canister 230. If any of the conditions may not be satisfied, the pump assembly 150 can be determined to be operating with the canister 230. The order of the process 600 determining the conditions in blocks 602, 608, and 610 can be changed from what is illustrated in FIG. 6.

In other embodiments, the canister detection process 600 can depend on one or two conditions for determining whether the pump assembly 150 may be operating with or without the canister 230. For example, the canister detection process 600 can depend on the determinations in either (i) block 602 and not blocks 608 and 610, (ii) block 608 and not blocks 602 and 610, (iii) block 610 and not block 602 and 608, (iv) blocks 602 and 608 and not block 604, (v) in blocks 602 and 610 and not block 608, or (vi) blocks 608 and 610 and not block 602 for determining whether the pump assembly 150 may be operating with or without the canister 230. The pump assembly 150 can, for instance, discard the determination in the unused block, not perform the determination in the unused block, or not perform the detection usable to perform the determination. When any of the conditions may not be satisfied, the pump assembly 150 can, as described previously, be determined to be operating with the canister 230.

In yet other embodiments, the canister detection process 600 can depend on one or more other conditions for determining whether the pump assembly 150 may be operating with or without the canister 230. For example, the canister detection process 600 can depend on one or more of (i) a user controllable toggle switch indicating whether the pump assembly 150 is operating with or without the canister 230, (ii) a proximity sensor like an RFID sensor of the pump assembly 150 indicating whether the canister 230 is in the vicinity of the housing 200 of the pump assembly 150, (iii) a pressure sensor indicating whether canister tabs used to secure the canister 230 to the housing 200 of the pump assembly 150 are engaged and thus securing the canister 230, (iv) one or more previous determinations of whether the pump assembly 150 operated with or without the canister 230, and (v) a duration of time that one or more indications indicate that the pump assembly 150 may be operating with or without the canister 230, such as the duration of the time the user controllable toggle switch is toggled, the proximity sensor indicates presence of the canister, or the pressure sensor indicates presence of the canister. The conditions can be evaluated by approaches, such as by majority of conditions control, weighting conditions to favor user inputs or automatic detections, or varying importance of conditions by patient, type of therapy, or time of day, to arrive at the final determination of whether the pump assembly 150 may be operating with or without the canister 230. One of the advantages of performing the canister detection process 600 for automatically detecting presence of a canister is that it does not involve user interaction or rely on the accuracy of such interaction or necessitate the use of additional canister detection sensors, such as RFID, proximity, etc., which would add cost and complexity.

The canister detection process 600 may not favor determining that the pump assembly 150 is operating with the canister 230 in some implementations. Instead, the canister detection process 600 may favor determining that the pump assembly 150 is operating without the canister 230 and determine that the pump assembly 150 is operating with the canister 230 when more than one condition indicate presence of the canister 230, such as two conditions, three conditions, or more than three conditions.

Figure 7:
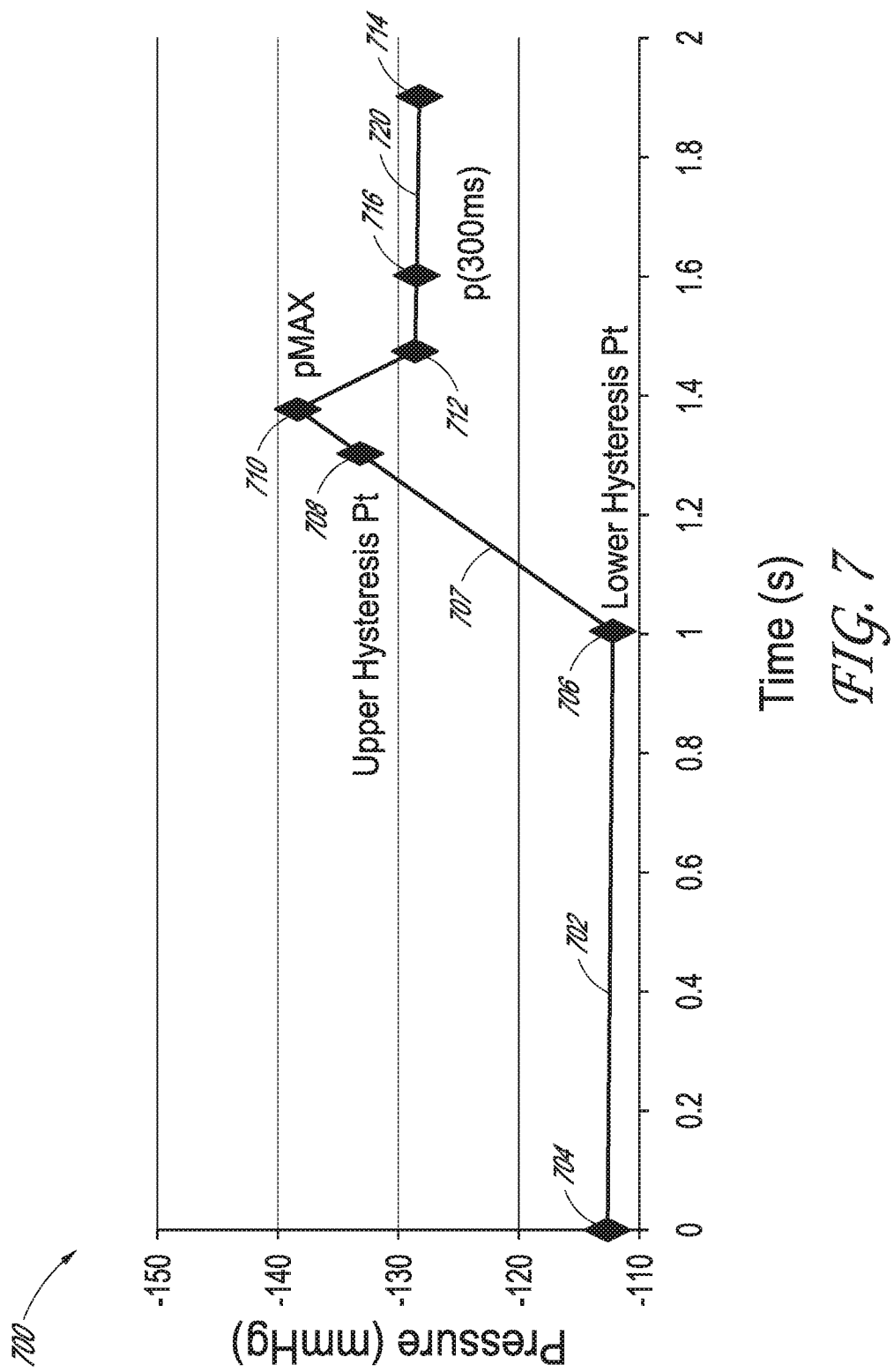
FIG. 7 is a graph depicting values usable in the canister detection process of FIG. 6 according to some embodiments.

FIG. 7 is a graph 700 depicting values usable by the canister detection process 600 according to some embodiments. The graph 700 illustrates pressure in the TNP system 100, such as at a pump head or inlet of the source of negative pressure 210, while the pump assembly 150 is operating in the maintenance mode 450. The graph 700 illustrates variance in negative pressure in the fluid flow path over time.

The pump assembly 150 can operate in the monitor state 452 (with the negative pressure source being deactivated) from point 704 until point 706. During this period, the pressure may begin to gradually decay, as illustrated by the line 702, due to the source of negative pressure 210 being deactivated and the existence of minor leakages in the TNP system 100. Beginning at point 706, the pump assembly 150 can transition to the MPD state 454 and reactivate the source of negative pressure 210 to lower the pressure as illustrated by line 707. Point 706 can be referred to as the lower hysteresis point. After negative pressure under the dressing reaches a target pressure at point 708, the pump assembly 150 can switch back to the monitor state 452 and deactivate the source of negative pressure 210. Point 708 can be referred to as the upper hysteresis point. The pressure in the fluid flow path can continue toward an even lower level after the point 708 until point 710 due to a pressure overshoot in the TNP system 100. The pressure at point 710 can be referred to as the maximum pressure because the pressure at point 710 is a local maximum negative pressure in the graph 700. The negative pressure begins to decay relatively quickly after point 710 until point 712 as the pressure overshoot stabilizes as illustrated by the line 720. After point 712, the pressure again may begin to gradually decay until point 714 due to the existence of minor leakages in the TNP system 100. Point 716 can be a sample point about 300 ms after point 708. Although point 716 is set at about 300 ms after point 708, in other embodiments, the sample point can be a point anywhere along the line 720 after point 712 and before the beginning of a next MPD state 454, at a time when the pressure gradually decays due to the existence of minor leakages in the TNP system 100.

In one example, the canister detection process 600 can determine the level of activity of the source of negative pressure 210 based on the duration of time that the source of negative pressure is on from point 706 to point 708. For instance, the canister detection process 600 can determine the level of activity of the source of negative pressure 210 by comparing (i) the duration of time from point 706 to point 708 relative to (ii) the duration of time that the pump is off from point 708 until the beginning of a next MPD state 454. In another example, the canister detection process 600 can determine the peak pressure to be the pressure difference between point 710 and point 708. In yet another example, the canister detection process 600 can determine the peak pressure to be the pressure at point 710. In yet another example, the canister detection process 600 can determine the settling pressure to be the pressure difference between point 708 and point 716.

Blockage Detection Process

Figure 8:
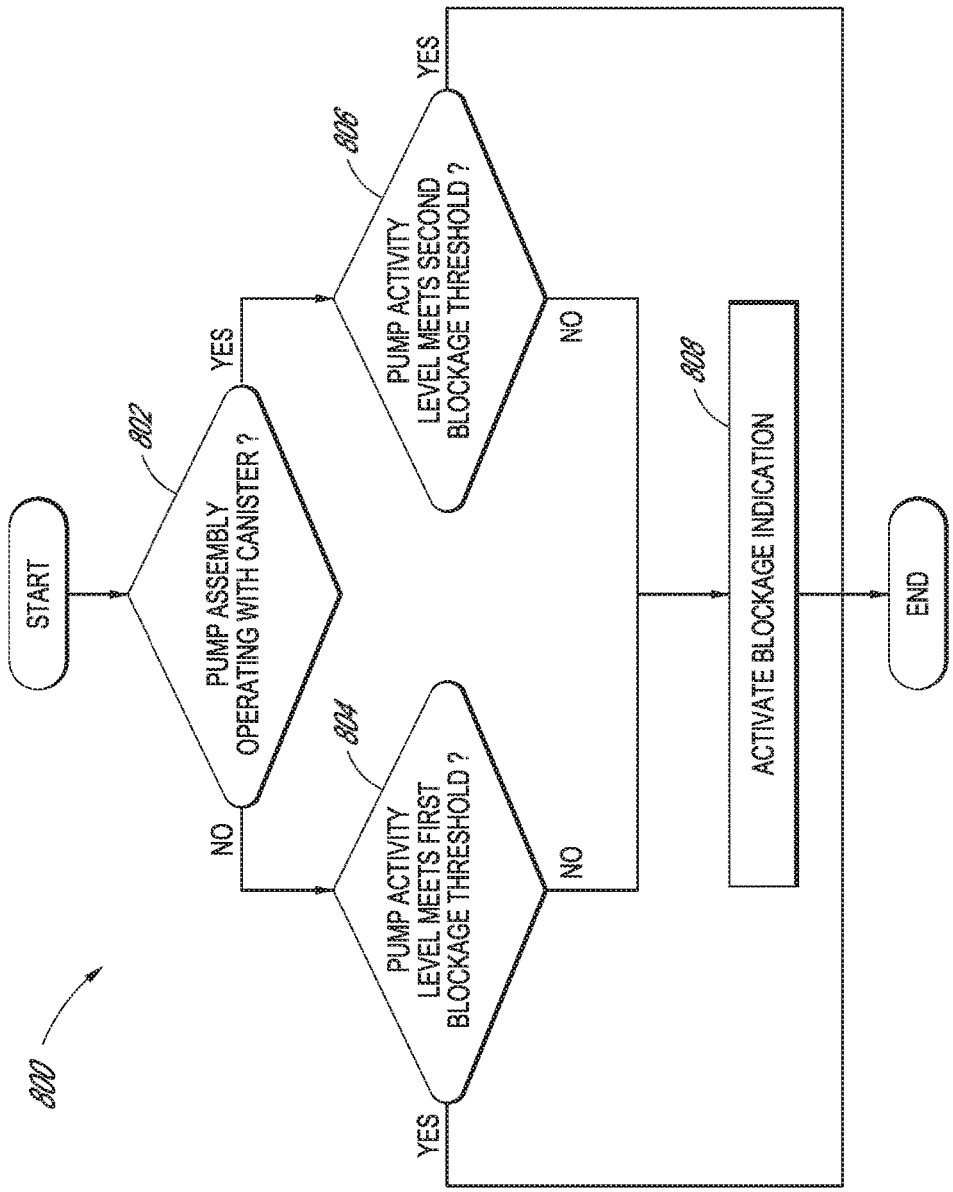
FIG. 8 illustrates a blockage detection process performable by the pump assembly of FIG. 1 according to some embodiments.

FIG. 8 illustrates a blockage detection process 800 performable by a device, such as the pump assembly 150, according to some embodiments. For convenience, the blockage detection process 800 is described in the context of the TNP system 100, but may instead be implemented in other systems described herein or by other computing systems not shown. The blockage detection process 800 can be (i) performed by the controller 302 when the pump assembly 150 is operating in the maintenance mode 450 (or IPD mode 414), (ii) used to determine the existence of a blockage for any of the pump embodiments disclosed herein, and (iii) alert the user if the blockage has occurred so that the user can take remedial actions to relieve or remove the blockage. The blockage detection process 800 can desirably enable the more accurate detection of blockages in the TNP system 100, such as in the fluid flow path between the pump assembly 150 and the wound dressing, because the blockage detection process 800 can account for expected pump activity level differences when the pump assembly 150 is operating with or without the canister 230 under blockage conditions.

The blockage detection process 800 can be implemented based at least on the understanding that the pump assembly 150 operates in an environment with a leak and that the characteristics of the leak may vary depending on whether the pump assembly 150 is operating with or without the canister 230.

For example, when the assembly 150 is operating with the canister 230 and the foam or gauze dressing, how often the source of negative pressure 210 operates to maintain pressure, such as indicated by an on/off time of the source of negative pressure 210, can indicate a blockage in the fluid flow path. This can be because the fluid flow path can include a controlled leak (for instance, a leak of around 10 ccm), which ensures or guarantees a certain minimum level of fluid flow. In some embodiments, a port on the dressing can have dual lumen tubing with one lumen used for a controlled leak path to vent the wound dressing and another lumen for exudate removal to the canister 230. The controlled leak can, in turn, increase drive up a minimum pump on duty cycle. The TNP system 100 can be intended for relatively low exudating wounds (for instance, around 64.8 mL/day) and the leak may be able to clear temporary blockages in the fluid flow path. However, some blockages may not be cleared, such as for example if the fluid flow rate is too high.

As another example, when the assembly 150 is operating without the canister 230 and with the absorbent dressing, exudate may not enter the fluid flow path due to a hydrophobic filter in the absorbent dressing. While there may not be a controlled leak in the fluid flow path, a small amount of leaks can be naturally observed, and a certain minimum level of fluid flow can be anticipated. In turn, a minimum amount of maintenance cycles of the source of negative pressure 210 can be triggered when the fluid flow path is clear of a blockage.

When a sufficient blockage is present in the fluid flow path, minimum level of fluid flow may not be maintained in the fluid flow path. In turn, the negative pressure source may not meet an expected minimum activity level that corresponds to maintenance of the minimum level of fluid flow in the fluid flow path. As explained herein, this condition can be utilized for blockage detection in some embodiments.

At block 802, the blockage detection process 800 can determine whether the pump assembly 150 is operating with or without the canister 230. The process 800 can, for example, perform the canister detection process 600 or reference one or more of the parameters set at blocks 606 and 614 to determine whether the pump assembly 150 is operating with or without the canister 230.

In response to the blockage detection process 800 determining that the pump assembly 150 is not operating with the canister 230, the blockage detection process 800 moves to block 804, and the blockage detection process 800 determines whether a pump activity level of the pump assembly 150 meets a first blockage threshold. The pump activity level can be determined as described with respect to block 602 of the canister detection process 600. The first blockage threshold can be a level of activity of the pump assembly 150, such as of the source of negative pressure 210, at or below which the minimum level of fluid flow cannot be maintained in the fluid flow path when the pump assembly 150 is operating without the canister 230. The first blockage threshold can, in some implementations, be a duty cycle percentage used to control the source of negative pressure 210, such as duty cycle percentage ranging from 0.025% or less to 0.5% or more (for example, about 0.05%, 0.25%, 0.1%, etc.). The first blockage threshold can be set at pump assembly manufacture, experimentally determined during pump assembly testing, or configurable by a user, in some implementations.

In response to the blockage detection process 800 determining that the pump activity level does not meet the first blockage threshold, at block 808, the blockage detection process 800 can activate a blockage indication of the one or more indicators 204 to notify a user that the blockage is detected. Additionally or alternatively, the blockage detection process 800 can deactivate the negative pressure source in order to conserve power. In response to the blockage detection process 800 determining that the pump activity level meets the first blockage threshold, the blockage detection process 800 can end.

In response to the blockage detection process 800 determining that the pump assembly 150 is operating with the canister 230, the blockage detection process 800 moves to block 806, and the blockage detection process 800 determines whether a pump activity level of the pump assembly 150 meets a second blockage threshold. The pump activity level can be determined as described with respect to block 602 of the canister detection process 600. The second blockage threshold can be a level of activity of the pump assembly 150, such as of the source of negative pressure 210, at or below which the minimum level of fluid flow cannot be maintained in the fluid flow path when the pump assembly 150 is operating with the canister 230. The second blockage threshold can, in some implementations, be a duty cycle percentage used to control the source of negative pressure 210, such as duty cycle percentage ranging from 0.25% or less to 5% or more (for example, about 0.5%, 1%, 2.5%, etc.). The second blockage threshold can be set at pump assembly manufacture, experimentally determined during pump assembly testing, or configurable by a user, in some implementations. In some embodiments, the second blockage threshold can be different from the first blockage threshold, for example, the second blockage threshold can be greater than the first blockage threshold.

In response to the blockage detection process 800 determining that the pump activity level does not meet the second blockage threshold, at block 808, the blockage detection process 800 can activate a blockage indication of the one or more indicators 204 to notify a user that the blockage is detected. Additionally or alternatively, the blockage detection process 800 can deactivate the negative pressure source in order to conserve power. In response to the blockage detection process 800 determining that the pump activity level meets the second blockage threshold, the blockage detection process 800 can end.

In further embodiments, one or more other factors (for example, excessive peak pressure in the fluid flow path) can be further used in combination with the first and second blockages thresholds to determine when to activate the blockage indication. Such other factors can enable the blockage indication to be activated with even greater accuracy.

Leak Detection and Clearing Processes

Figure 9:
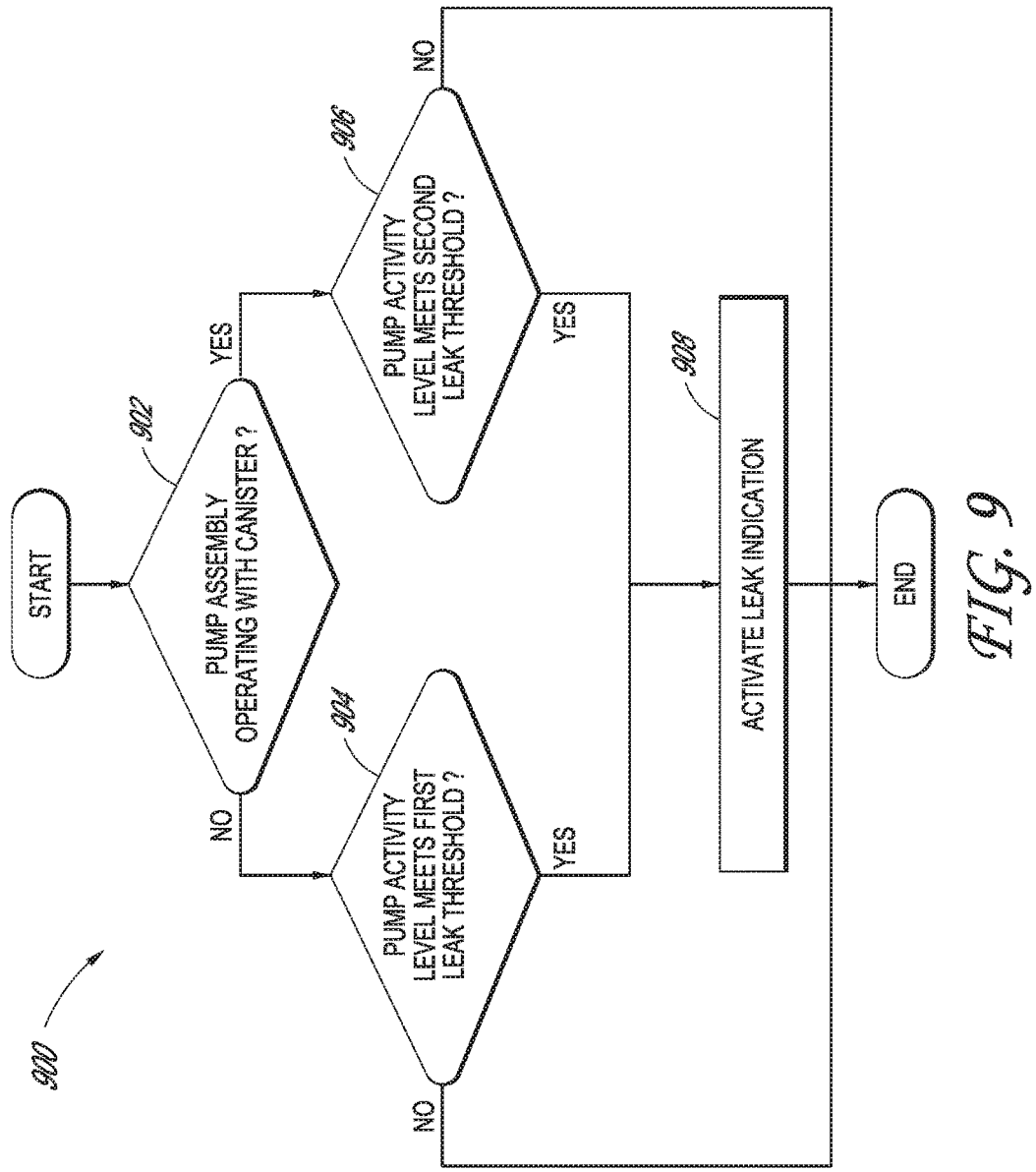
FIG. 9 illustrates a leak detection process performable by the pump assembly of FIG. 1 according to some embodiments.

FIG. 9 illustrates a leak detection process 900 performable by a device, such as the pump assembly 150, according to some embodiments. For convenience, the leak detection process 900 is described in the context of the TNP system 100, but may instead be implemented in other systems described herein or by other computing systems not shown. The leak detection process 900 can be (i) performed by the controller 302 when the pump assembly 150 is operating in the maintenance mode 450 (or IPD mode 414), (ii) used to determine the existence of a leak for any of the pump embodiments disclosed herein, and (iii) alert the user if the leak has occurred so that the user can take remedial actions to relieve or remove the leak. The leak detection process 900 can desirably enable the more accurate detection of leaks in the TNP system 100, such as in the fluid flow path between the pump assembly 150 and the wound dressing like in the wound dressing, because the leak detection process 900 can account for expected pump activity level differences when the pump assembly 150 is operating with or without the canister 230 under leak conditions.

The leak detection process 900 can be implemented based at least on the understanding the pump assembly 150 operates in an environment with a leak and that the characteristics of the leak may vary depending on whether the pump assembly 150 is operating with or without the canister 230. A greater leak can be expected during normal operation of the pump assembly 150 when the pump assembly 150 is operating with the canister 230 than when the pump assembly 150 is operating without the canister 230. Moreover, when a desired pressure for therapy may not be obtained due to an excessive leak, how often the source of negative pressure 210 operates to maintain pressure, such as indicated by an on/off time of the source of negative pressure 210, can indicate the excessive leak in the fluid flow path. That is, when a significant or excessive leak is present in the fluid flow path, the negative pressure source may be active for excessive amount of time (or be working "too hard") in the attempt to reach and maintain the target pressure levels under the wound dressing. This can be utilized for leak detection.

At block 902, the leak detection process 900 can determine whether the pump assembly 150 is operating with or without the canister 230. The leak detection process 900 can, for example, perform the canister detection process 600 or reference one or more of the parameters set at blocks 606 and 614 to determine whether the pump assembly 150 is operating with or without the canister 230.

In response to the leak detection process 900 determining that the pump assembly 150 is not operating with the canister 230, the leak detection process 900 moves to block 904, and the leak detection process 900 determines whether a pump activity level of the pump assembly 150 meets a first leak threshold. The pump activity level can be determined as described with respect to block 602 of the canister detection process 600. The first leak threshold can be a level of activity of the pump assembly 150, such as of the source of negative pressure 210, above which is indicative of an excessive leak in the fluid flow path when the pump assembly 150 is operating without the canister 230. The first leak threshold, in some implementations, can be a duty cycle percentage used to control the source of negative pressure 210, such as duty cycle percentage ranging from 1% or less to 15% or more (for example, about 1%, 2%, 3%, 4%, 5%, 6%, 10%, etc.). The first leak threshold can be set at pump assembly manufacture, experimentally determined during pump assembly testing, or configurable by a user, in some implementations.

In response to the leak detection process 900 determining that the pump activity level meets the first leak threshold, at block 908, the leak detection process 900 can activate a leak indication of the one or more indicators 204 to notify a user that the leak is detected. Additionally or alternatively, the leak detection process 900 can deactivate the negative pressure source in order to conserve power. In response to the leak detection process 900 determining that the pump activity level does not meet the first leak threshold, the leak detection process 900 can end.

In response to the leak detection process 900 determining that the pump assembly 150 is operating with the canister 230, the leak detection process 900 moves to block 906, and the leak detection process 900 determines whether a pump activity level of the pump assembly 150 meets a second leak threshold. The pump activity level can be determined as described with respect to block 602 of the canister detection process 600. The second leak threshold can be a level of activity of the pump assembly 150, such as of the source of negative pressure 210, above which is indicative of an excessive leak in the fluid flow path when the pump assembly 150 is operating with the canister 230. The second leak threshold can, in some implementations, be a duty cycle percentage used to control the source of negative pressure 210, such as duty cycle percentage ranging from 3% or less to 25% or more (for example, about 5%, 10%, 12%, 15%, 20%, etc.). The second leak threshold can be set at pump assembly manufacture, experimentally determined during pump assembly testing, or configurable by a user, in some implementations. In some embodiments, the second leak threshold can be different from the first leak threshold, for example, the second leak threshold can be greater than the first leak threshold.

In response to the leak detection process 900 determining that the pump activity level meets the second leak threshold, at block 908, the leak detection process 900 can activate a leak indication of the one or more indicators 204 to notify a user that the leak is detected. Additionally or alternatively, the leak detection process 900 can deactivate the negative pressure source in order to conserve power. In response to the leak detection process 900 determining that the pump activity level does not meet the second leak threshold, the leak detection process 900 can end.

In further embodiments, one or more other factors (for example, a measured pressure in the fluid flow path indicating an inability to reach a desired pressure for therapy) can be further used in combination with the first and second leak thresholds to determine when to activate the leak indication. Such other factors can enable the leak indication to be activated with even greater accuracy.

Figure 10:
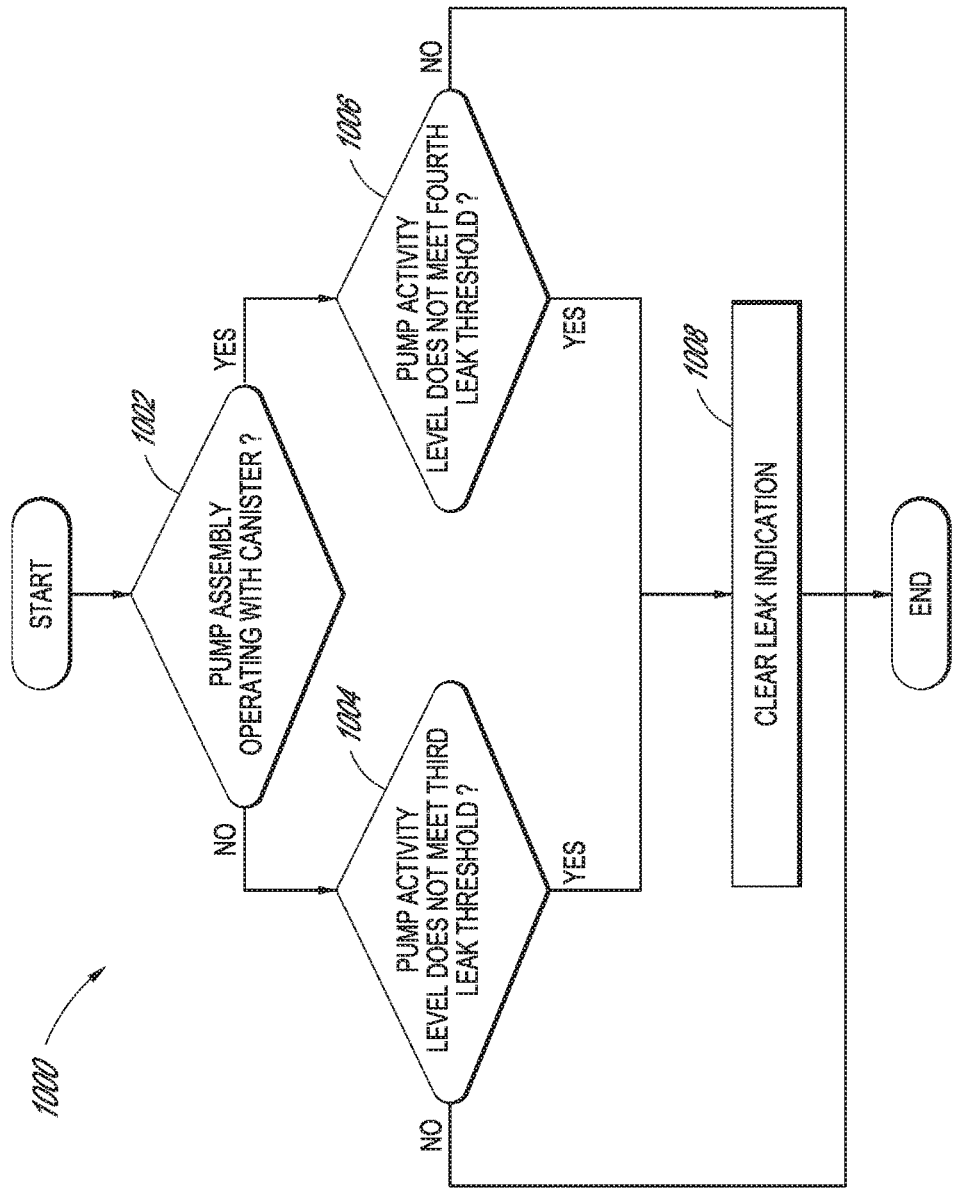
FIG. 10 illustrates a leak indication clearing process performable by the pump assembly of FIG. 1 according to some embodiments.

FIG. 10 illustrates a leak indication clearing process 1000 performable by a device, such as the pump assembly 150, according to some embodiments. For convenience, the leak indication clearing process 1000 is described in the context of the TNP system 100, but may instead be implemented in other systems described herein or by other computing systems not shown. The leak indication clearing process 1000 can be (i) performed by the controller 302 when the pump assembly 150 is operating in the leak state 416, (ii) used to determine that a leak has been cleared for any of the pump embodiments disclosed herein, and (iii) deactivate an alert to the user that the leak has occurred. The indication leak clearing process 1000 can desirably enable the more accurate clearing of indications by the process of leaks in the TNP system 100, such as in the fluid flow path between the pump assembly 150 and the wound dressing, because the leak indication clearing process 1000 can account for expected pump activity level differences when the pump assembly 150 is operating with or without the canister 230 under leak conditions. The leak indication clearing process 1000 can be implemented based at least on similar understandings as described with respect to the leak detection process 900.

At block 1002, the leak indication clearing process 1000 can determine whether the pump assembly 150 is operating with or without the canister 230. The leak indication clearing process 1000 can, for example, perform the canister detection process 600 or reference one or more of the parameters set at blocks 606 and 614 to determine whether the pump assembly 150 is operating with or without the canister 230.

In response to the leak indication clearing process 1000 determining that the pump assembly 150 is not operating with the canister 230, the leak indication clearing process 1000 moves to block 1004, and the leak indication clearing process 1000 determines whether a pump activity level of the pump assembly 150 does not meet a third leak threshold. The pump activity level can be determined as described with respect to block 602 of the canister detection process 600. The third leak threshold can be a level of activity of the pump assembly 150, such as of the source of negative pressure 210, at or below which is indicative of no excessive leak in the fluid flow path when the pump assembly 150 is operating without the canister 230. The third leak threshold can, in some implementations, be a duty cycle percentage used to control the source of negative pressure 210, such as duty cycle percentage ranging from 1% or less to 15% or more (for example, about 1%, 2%, 2.5%, 3%, 5%, 10%, etc.). The third leak threshold can be set at pump assembly manufacture, experimentally determined during pump assembly testing, or configurable by a user, in some implementations. In some embodiments, the third leak threshold can be different from the first leak threshold, or the third leak threshold can be smaller than the first leak threshold.

In response to the leak indication clearing process 1000 determining that the pump activity level does not meet the third leak threshold, at block 1008, the leak indication clearing process 1000 can clear a leak indication of the one or more indicators 204 to notify a user that the leak has been addressed. In response to the leak indication clearing process 1000 determining that the pump activity level meets the third leak threshold, the leak indication clearing process 1000 can end.

In response to the leak indication clearing process 1000 determining that the pump assembly 150 is operating with the canister 230, the leak indication clearing process 1000 moves to block 1006, and the leak indication clearing process 1000 determines whether a pump activity level of the pump assembly 150 does not meet a fourth leak threshold. The pump activity level can be determined as described with respect to block 602 of the canister detection process 600. The fourth leak threshold can be a level of activity of the pump assembly 150, such as of the source of negative pressure 210, below which is indicative of no excessive leak in the fluid flow path when the pump assembly 150 is operating without the canister 230. The fourth leak threshold can, in some implementations, be a duty cycle percentage used to control the source of negative pressure 210, such as duty cycle percentage ranging from 3% or less to 25% or more (for example, about 5%, 8%, 10%, 12%, 20%, etc.). The fourth leak threshold can be set at pump assembly manufacture, experimentally determined during pump assembly testing, or configurable by a user, in some implementations. In some embodiments, the fourth leak threshold can be different from the third leak threshold, or the fourth leak threshold can be greater than the third leak threshold. Moreover, in some embodiments, the fourth leak threshold can be different from the second leak threshold, or the fourth leak threshold can be smaller than the second leak threshold.

In response to the leak indication clearing process 1000 determining that the pump activity level does not meet the fourth leak threshold, at block 1008, the leak indication clearing process 1000 can clear a leak indication of the one or more indicators 204 to notify a user that the leak has been addressed. In response to the leak indication clearing process 1000 determining that the pump activity level meets the fourth leak threshold, the leak indication clearing process 1000 can end.

In further embodiments, one or more other factors (for example, a measured pressure in the fluid flow path indicating a desired pressure for therapy can be reached) can be further used in combination with the third and fourth leak thresholds to determine when to clear the leak indication. Such other factors can enable the leak indication to be cleared with even greater accuracy.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
a negative pressure source configured to be coupled to a dressing placed over a wound via a first fluid flow path or a second fluid flow path, the first fluid flow path comprising at least one lumen and not comprising a canister configured to store fluid removed from the wound, and the second fluid flow path comprising at least one lumen and the canister; and
a controller configured to:
detect whether the negative pressure source is coupled via the first or second fluid flow path to the dressing,
in response to detecting that the negative pressure source is coupled to the dressing via the first fluid flow path, select a first mode of operation and cause the negative pressure source to provide negative pressure via the first fluid flow path to the dressing in accordance with the first mode of operation; and
in response to detecting that the negative pressure source is coupled to the dressing via the second fluid flow path, select a second mode of operation different from the first mode of operation and cause the negative pressure source to provide negative pressure via the second fluid flow path to the dressing in accordance with the second mode of operation.

2. The negative pressure wound therapy system of claim 1, wherein the controller is configured to control one or more operations of the negative pressure source differently in the first or second modes of operation.

3. The negative pressure wound therapy system of claim 1, wherein the first mode of operation comprises canisterless mode of operation and the second mode of operation comprises canister mode of operation.

4. The negative pressure wound therapy system of claim 1, further comprising a switch configured to indicate whether the negative pressure source is coupled to the dressing via the first or second fluid flow path.

5. The negative pressure wound therapy system of claim 4, wherein the switch comprises a toggle switch.

6. The negative pressure wound therapy system of claim 1, further comprising a sensor configured to indicate whether the negative pressure source is coupled to the dressing via the first or second fluid flow path.

7. The negative pressure wound therapy system of claim 6, wherein the sensor comprises a proximity sensor.

8. The negative pressure wound therapy system of claim 6, wherein the sensor comprises a pressure sensor.

9. The negative pressure wound therapy system of claim 6, wherein the sensor is configured to indicate whether the canister is secured to a housing enclosing the negative pressure source.

10. The negative pressure wound therapy system of claim 9, wherein the sensor is configured to detect that a tab of the canister is engaged with the housing.

11. A method of controlling operation of a negative pressure wound therapy system, the method comprising:

detecting, by a controller of the negative pressure wound therapy system, whether a negative pressure source of the negative pressure wound therapy system is coupled via a first or second fluid flow path to a dressing placed over a wound, the first fluid flow path comprising at least one lumen and not comprising a canister configured to store fluid removed from the wound, and the second fluid flow path comprising at least one lumen and the canister;
in response to detecting that the negative pressure source is coupled via the first fluid flow path, selecting, by the controller, a first mode of operation in which the system is configured to provide negative pressure to the dressing with the negative pressure source via the first fluid flow path in accordance with the first mode of operation;
in response to detecting that the negative pressure source is coupled via the second fluid flow path, selecting, by the controller, a second mode of operation different from the first mode of operation in which the system is configured to provide negative pressure to the dressing with the negative pressure source via the second fluid flow path in accordance with the second mode of operation; and
by the controller, causing provision of negative pressure with the negative pressure source according to the selected mode of operation.

12. The method of claim 11, wherein the first mode of operation comprises canisterless mode of operation and the second mode of operation comprises canister mode of operation.

13. The method of claim 11, wherein the detecting comprises interrogating a switch configured to indicate whether the negative pressure source is coupled to the dressing via the first or second fluid flow path.

14. The method of claim 13, wherein the switch is configured to be in a first position when the negative pressure source is coupled to the dressing via the first fluid flow path and in a second position different from the first position when the negative pressure source is coupled to the dressing via the second fluid flow path.

15. The method of claim 13, wherein the switch comprises a toggle switch.

16. The method of claim 11, wherein the detecting comprises determining with a sensor whether the negative pressure source is coupled to the dressing via the first or second fluid flow path.

17. The negative pressure wound therapy system of claim 16, wherein the sensor comprises a proximity sensor.

18. The negative pressure wound therapy system of claim 16, wherein the sensor comprises a pressure sensor.

19. The negative pressure wound therapy system of claim 16, wherein the sensor is configured to determine whether the canister is secured to a housing of the negative pressure source.

20. The negative pressure wound therapy system of claim 16, wherein the sensor is configured to detect that a tab of the canister is engaged with a housing of the negative pressure wound therapy system.

* * * * *

UNITED STATES PATENT AND TRADEMARK OFFICE
CERTIFICATE OF CORRECTION

| | |
|---|---|
| PATENT NO. | : 11,426,509 B2 |
| APPLICATION NO. | : 16/206860 |
| DATED | : August 30, 2022 |
| INVENTOR(S) | : Eric Edward Adams |

It is certified that error appears in the above-identified patent and that said Letters Patent is hereby corrected as shown below:

On the Title Page

Column 1, Item (72), under Inventors, delete "Saint Petersberg, FL" and insert --Saint Petersburg, FL--.

On Page 3, Column 2, Line 3, Item (56), under Other Publications, delete "Reporton" and insert --Report on--.

In the Specification

In Column 1, Line 7, under CROSS-REFERENCE TO RELATED APPLICATIONS, delete "This application is a continuation of U.S. patent" and insert --This application is a divisional of U.S. patent--.

In Column 11, Line 39, delete "can by" and insert --can be--.

In Column 14, Line 27, delete "can" and insert --can be--.

In Column 18, Line 19, delete "414" and insert --412--.

In Column 18, Line 55, delete "414" and insert --416--.

In the Claims

In Column 40, Line 48, under Claim 17, delete "negative pressure wound therapy system" and insert --method--.

In Column 40, Line 50, under Claim 18, delete "negative pressure wound therapy system" and insert --method--.

Signed and Sealed this
Fourteenth Day of March, 2023

Katherine Kelly Vidal
*Director of the United States Patent and Trademark Office*

In Column 40, Line 52, under Claim 19, delete "negative pressure wound therapy system" and insert --method--.

In Column 40, Line 56, under Claim 20, delete "negative pressure wound therapy system" and insert --method--.